(12) United States Patent
Chen et al.

(10) Patent No.: US 12,699,087 B2
(45) Date of Patent: Aug. 4, 2026

(54) MONITORING OF IN VITRO PROTEIN SYNTHESIS

(71) Applicant: Nuclera Ltd, Cambridge (GB)

(72) Inventors: Michael Chun Hao Chen, Cambridge (GB); Sihong Chen, Cambridge (GB); Stephanie Reikine, Cambridge (GB); Richard J. Paolini, Jr., Billerica, MA (US); Luke Slominski, Billerica, MA (US); Sumit Kalsi, Cambridge (GB); Atanas Yordanov Georgiev, Cambridge, MA (US); Chiara Gandini, Cambridge (GB)

(73) Assignee: Nuclera Ltd, Cambridge (GB)

( * ) Notice: Subject to any disclaimer, the term of this patent is extended or adjusted under 35 U.S.C. 154(b) by 624 days.

(21) Appl. No.: 18/021,945

(22) PCT Filed: Aug. 18, 2021

(86) PCT No.: PCT/GB2021/052140
§ 371 (c)(1),
(2) Date: Feb. 17, 2023

(87) PCT Pub. No.: WO2022/038353
PCT Pub. Date: Feb. 24, 2022

(65) Prior Publication Data
US 2024/0044878 A1 Feb. 8, 2024

(30) Foreign Application Priority Data
Aug. 21, 2020 (GB) ...................................... 2013063

(51) Int. Cl.
| | |
|---|---|
| *G01N 33/542* | (2006.01) |
| *B01L 3/00* | (2006.01) |
| *G01N 33/68* | (2006.01) |

(52) U.S. Cl.
CPC ...... *G01N 33/542* (2013.01); *B01L 3/502784* (2013.01); *G01N 33/6803* (2013.01)

(58) Field of Classification Search
CPC ............ B01L 3/502784; G01N 33/542; G01N 33/6803
See application file for complete search history.

(56) References Cited

U.S. PATENT DOCUMENTS

| | | | |
|---|---|---|---|
| 7,851,184 B2 | 12/2010 | Pollack et al. |
| 8,364,315 B2 | 1/2013 | Sturmer et al. |

(Continued)

FOREIGN PATENT DOCUMENTS

| | | |
|---|---|---|
| CN | 101472940 A | 7/2009 |
| CN | 111107937 A | 5/2020 |

(Continued)

OTHER PUBLICATIONS

Avilov et al., Fluorescence protein complementation in microscopy: applications beyond detecting bi-molecular interactions. Methods Appl Fluoresc. Nov. 20, 2018;7(1):012001, 13 pages.

(Continued)

*Primary Examiner* — Jennifer Wecker
(74) *Attorney, Agent, or Firm* — McCarter & English, LLP

(57) ABSTRACT

Provided herein are methods, and compositions for the real-time detection of protein synthesis. The methods are applicable to monitoring on a microfluidic device.

20 Claims, 12 Drawing Sheets
Specification includes a Sequence Listing.

No fluorescence          Fluorescence

(56)                  References Cited

U.S. PATENT DOCUMENTS

| | | | |
|---|---|---|---|
| 9,310,372 B2 * | 4/2016 | Patterson ............ G01N 33/577 |
| 2006/0228708 A1 | 10/2006 | Smilansky |
| 2013/0271153 A1 | 10/2013 | Hadwen |
| 2016/0230203 A1 | 8/2016 | Dresios et al. |
| 2018/0141049 A1 | 5/2018 | Jebrail et al. |
| 2019/0111433 A1 | 4/2019 | French |
| 2019/0262829 A1 | 8/2019 | Umapathi |
| 2019/0352687 A1 | 11/2019 | Milton et al. |
| 2021/0016283 A1 | 1/2021 | Zhang et al. |
| 2023/0042211 A1 | 2/2023 | Chen et al. |
| 2023/0092310 A1 | 3/2023 | Chen et al. |

FOREIGN PATENT DOCUMENTS

| | | |
|---|---|---|
| CN | 112136205 A | 12/2020 |
| EP | 1649025 A2 | 4/2006 |
| GB | 2602231 A | 6/2022 |
| GB | 2602231 B | 12/2022 |
| JP | 2010-506136 A | 2/2010 |
| JP | 2019-516368 A | 6/2019 |
| JP | 2020-506721 A | 3/2020 |
| JP | 2023-513313 A | 3/2023 |
| WO | 2007/120241 A2 | 10/2007 |
| WO | 2008/063227 A2 | 5/2008 |
| WO | 2009/111723 A1 | 9/2009 |
| WO | 2015/063767 A1 | 5/2015 |
| WO | 2016/048994 A2 | 3/2016 |
| WO | 2018/132440 A1 | 7/2018 |
| WO | 2019/030155 A1 | 2/2019 |
| WO | 2019/153067 A1 | 8/2019 |
| WO | 2019/169076 A1 | 9/2019 |
| WO | 2021/161048 A1 | 8/2021 |
| WO | 2025/017327 A2 | 1/2025 |
| WO | 2025/037122 A1 | 2/2025 |
| WO | 2025/240570 A1 | 11/2025 |

OTHER PUBLICATIONS

Ayoubi-Joshaghani et al., Cell-free protein synthesis: The transition from batch reactions to minimal cells and microfluidic devices. Biotechnol Bioeng. Apr. 2020;117(4):1204-1229.

Bansal et al., Axisymmetric and Nonaxisymmetric Oscillations of Sessile Compound Droplets in an Open Digital Microfluidic Platform. Langmuir. Oct. 17, 2017;33(41):11047-11058.

Cho et al., Droplet-based microfluidic platform for high-throughput, multi-parameter screening of photosensitizer activity. Anal Chem. Sep. 17, 2013;85(18):8866-72.

Courtois et al., An integrated device for monitoring time-dependent in vitro expression from single genes in picolitre droplets. Chembiochem. Feb. 15, 2008;9(3):439-46.

Fallah-Araghi et al., A completely in vitro ultrahigh-throughput droplet-based microfluidic screening system for protein engineering and directed evolution. Lab Chip. Mar. 7, 2012;12(5):882-91.

Fowler et al., Enhancement of Mixing by Droplet-Based Microfluidics. Proc IEEE Int Conf MEMS. pp. 97-100, Jan. 2002.

Geng et al., Antifouling digital microfluidics using lubricant infused porous film. Lab Chip. Jun. 25, 2019;19(13):2275-2283.

Kays, Observation and quantification of protein production in single living cells. Integrated Program in Neuroscience McGill University, Montreal. Thesis, 171 pages, Nov. 2016.

Saeki et al., Microcompartmentalized cell-free protein synthesis in semipermeable microcapsules composed of polyethylenimine-coated alginate. J Biosci Bioeng. Aug. 2014;118(2):199-204.

Xiao et al., Integration of cell-free protein synthesis and purification in one microfluidic chip for on-demand production of recombinant protein. Biomicrofluidics. Sep. 13, 2018;12(5):054102, 13 pages.

International Search Report and Written Opinion for Application No. PCT/GB2021/050362, dated May 17, 2021, 8 pages.

International Search Report and Written Opinion for Application No. PCT/GB2021/052140, dated Dec. 1, 2021, 12 pages.

Friddin et al., Cell-free protein expression systems in microdroplets: Stabilization of interdroplet bilayers. Biomicrofluidics. Feb. 6, 2013;7(1):14108, 12 pages.

U.S. Appl. No. 17/969,323, filed Oct. 19, 2022, US2023-0042211.

* cited by examiner

No fluorescence                    Fluorescence

A              B

C

MONITORING OF IN VITRO PROTEIN SYNTHESIS

CROSS-REFERENCE TO RELATED APPLICATIONS

This application is a U.S. national stage application filed under 35 U.S.C. 371, based on International Patent Application No. PCT/GB2021/052140, filed on Aug. 18, 2021, which claims priority to United Kingdom Patent Application No. 2013063.9, filed on Aug. 21, 2020. The entire contents of each of the aforementioned applications, including drawings and sequence listings, are incorporated herein by reference.

SEQUENCE LISTING

The instant application contains a Sequence Listing which has been submitted electronically in ASCII format and is hereby incorporated by reference in its entirety. Said ASCII copy, created on Feb. 17, 2023, is named 135815-01501_SL.txt, and is 12,494 bytes in size.

FIELD OF THE INVENTION

Provided herein are methods, and compositions for the on-device detection of protein synthesis. The methods are applicable to monitoring on a microfluidic device.

BACKGROUND TO THE INVENTION

When performing cell-free protein synthesis at microfluidic scale in a microfluidic device, such as a digital microfluidic device, it is useful to detect in real-time the proteins that are synthesized from said cell-free protein synthesis reaction. However, it is difficult to perform real-time detection of proteins in a cell-free protein synthesis reaction environment. The reaction contains many other proteins and biomolecules at high concentration, making non-specific protein detection via standard protein staining methods difficult (e.g., Coomassie Brilliant Blue G-250, SYPRO™ Ruby, Silver staining). Immunostaining or affinity-based purification followed by non-specific proteins staining are equally unhelpful as significant washing on a solid support must be performed to prevent background interference. As washing is known to be difficult in microfluidic and digital microfluidic devices, background interference may become debilitating.

Currently existing luminescent complementation approaches cannot achieve prolonged real-time detection in cell-free protein synthesis reactions, which often extend beyond 16 hours. This limit is due to a combination of reasons including $O_2$ consumption by the luminescence-generating enzyme that competes with cell-free protein synthesis $O_2$ requirements and temporary or permanent exhaustion of luminescent substrate over 3-24 hours of recombinant protein expression detection.

Proteins of interest may also be expressed as a fusion to a fluorescent protein, such as green fluorescent protein (GFP). However, GFP is a 26.9 kDa protein, which is the typical size for most fluorescent proteins. Tags of this size increase the total size of the protein of interest, especially if the protein of interest must be tagged with other large fusion proteins such as maltose-binding protein (MBP), which is 42.5 kDa. Given the average size of a human protein is ~52 kDa and the average size of an E. coli protein is ~35 kDa (Kim, Y. E. et al. Annu. Rev. Biochem. 2013. 82:323-355), the addition of a comparably sized fluorescent protein tag can significantly change the biological function and biophysical characteristics of a protein.

Many pieces of prior art disclose the use of sub-component tags for monitoring expression in a cellular system. For example U.S. Pat. No. 7,666,606 discloses protein-protein interaction detection systems using microdomains.

Schinn et al. Biotechnol. Bioeng 114 10 Oct. 2017 2412-2417. (https://onlinelibrary.wiley.com/doi/10.1002/bit.26305) discloses Rapid in vitro screening for the location-dependent effects of unnatural amino acids on protein expression and activity—Schinn—2017-Biotechnology and Bioengineering—Wiley Online Library.

SUMMARY

Here, we report the surprising discovery that a split peptide system can be engineered to perform in situ, fluorescence-based monitoring of the expression of a protein of interest in cell-free protein synthesis reactions. The monitoring can be performed on device during the course of the expression, so can be used in real-time or as an end-point measurement.

Disclosed herein is a method for the real-time monitoring of in vitro protein synthesis comprising a. in vitro transcription and translation of a protein of interest fused to a peptide tag; and b. monitoring the presence of the peptide tag using a further polypeptide which in the presence of the peptide tag produces a detectable signal.

Disclosed herein is a method for the monitoring of cell free protein synthesis in a droplet on a digital microfluidic device comprising a. cell free transcription and translation of a protein of interest fused to a peptide tag; and b. monitoring the presence of the peptide tag using a further polypeptide which in the presence of the peptide tag produces a detectable signal.

The use of the terms "in vitro" and "cell free" may be used interchangeably herein.

The detectable signal may be for example fluorescence or luminescence. The detectable signal may also be caused by the binding of a ligand to the complemented oligopeptide, peptide, or polypeptide tag fused to the protein of interest.

The detectable signal may also be caused by the binding of the polypeptide to the protein of interest fused to a His-tag.

Any in vitro transcription and translation may be used, for example extract-based systems derived from rabbit reticulocyte lysate, human lysate, Chinese Hamster Ovary lysate, a wheat germ, HEK293 lysate, E. coli lysate, yeast lysate.

Alternatively the in vitro transcription and translation may be assembled from purified components, for example a system of purified recombinant elements (PURE).

The in vitro transcription and translation may be coupled or uncoupled.

The peptide tag may be one component of a fluorescent protein and the further polypeptide a complementary portion of the fluorescent protein. The fluorescent protein could include sfGFP, GFP, eGFP, deGFP, frGFP, eYFP, eBFP, eCFP, Citrine, Venus, Cerulean, Dronpa, DsRED, mKate, mCherry, mRFP, FAST, SmURFP, miRFP670nano. For example the peptide tag may be $GFP_{11}$ and the further polypeptide $GFP_{1-10}$. The peptide tag may be one component of sfCherry. The peptide tag may be $sfCherry_{11}$ and the further polypeptide $sfCherry_{1-10}$. The peptide tag may be CFAST$_{11}$ or CFAST$_{10}$ and the further polypeptide NFAST in the presence of a hydroxybenzylidene rhodanine analog.

For example, the GFP1-10 polypeptide amino acid sequence could be derived from sfGFP:

MSKGEELFTGVVPILVELDGDVNGHKFSVRGEGEGDATNGKLTLKFICT

TGKLPVPWPTLVTTLTYGVQCFSRYPDHMKRHDFFKSAMPEGYVQERTI

SFKDDGTYKTRAEVKFEGDTLVNRIELKGIDFKEDGNILGHKLEYNFNS

HNVYITADKQKNGIKANFKIRHNVEDGSVQLADHYQQNTPIGDGPVLLP

DNHYLSTQSVLSKDPNEK

Alternatively, the GFP1-10 polypeptide amino acid sequence could be further mutated from the sequence above to become brighter more quickly upon complementation:

MSKGEELFTGVVPILVELDGDVNGHKFSVRGEGEGDATIGKLTLKFICT

TGKLPVPWPTLVTTLTYGVQCFSRYPDHMKRHDFFKSAMPEGYVQERTI

SFKDDGKYKTRAVVKFEGDTLVNRIELKGTDFKEDGNILGHKLEYNFNS

HNVYITADKQKNGIKANFTVRHNVEDGSVQLADHYQQNTPIGDGPVLLP

DNHYLSTQTVLSKDPNEK

The complementary GFP11 peptide amino acid sequence could be the following:

1.
KRDHMVLLEFVTAAGITGT

2.
KRDHMVLHEFVTAAGITGT

3.
KRDHMVLHESVNAAGIT

4.
RDHMVLHEYVNAAGIT

GFP11 or GFP1-10 can be fused to the protein of interest through an amino acid linker. In one embodiment, the oligopeptide, peptide, or polypeptide linker can be 0-50 amino acids.

For example, the sfCherry1-10 polypeptide amino acid sequence could be:

MEEDNMAIIKEFMRFKVHMEGSVNGHEFEIEGEGEGHPYEGTQTAKLKV

TKGGPLPFAWDILSPQFMYGSKAYVKHPADIPDYLKLSFPEGFTWERVM

NFEDGGVVTVTQDSSLODGEFIYKVKLLGTNFPSDGPVMQKKTMGWEAS

TERMYPEDGALKGEINQRLKLKDGGHYDAEVKTTYKAKKPVQLPGAYNV

DIKLDITSHNED

The complementary sfCherry11 peptide amino acid sequence could be:

YTIVEQYERAEGRHSTGG sfCherry11 or sfCherry1-10 can be fused to the protein of interest through an amino acid linker. In one embodiment, the oligopeptide, peptide, or polypeptide linker can be 0-50 amino acids.

For example, the NFAST polypeptide amino acid sequence could be:

MEHVAFGSEDIENTLAKMDDGOLDGLAFGAIQLDGDGNILQYNAAEGDI
TGRDPKQVIGKNFFKDVAPGTDSPEFYGKFKEGVASGNLNTMFEWMIPT
SRGPTKVKVHMKKALS

The complementary CFAST11 peptide amino acid sequence could be:

GDSYWVFVKRV

Or the complementary CFAST10 peptide amino acid sequence could be:

GDSYWVFVKR

NFAST, CFAST11, and/or CFAST10 can be fused to the protein of interest through an amino acid linker. In one embodiment, the oligopeptide, peptide, or polypeptide linker can be 0-50 amino acids.

The peptide tag may also be one component of a protein that forms a detectable substrate, such as a luminescent or colorigenic substrate. The protein could include beta-galactosidase, beta-lactamase, or luciferase.

The protein may be fused to multiple tags. For example the protein may be fused to multiple GFP$_{11}$ peptide tags and the synthesis occurs in the presence of multiple GFP$_{1-10}$ polypeptides. For example the protein may be fused to multiple sfCherry$_{11}$ peptide tags and the synthesis occurs in the presence of multiple sfCherry$_{1-10}$ polypeptides. The protein of interest may be fused to one or more sfCherry$_{11}$ peptide tags and one or more GFP$_{11}$ peptide tags and the synthesis occurs in the presence of one or more GFP$_{1-10}$ polypeptides and one or more sfCherry$_{1-10}$ polypeptides.

Any protein of interest may be synthesised. The protein may be an enzyme, for example a terminal deoxynucleotidyl transferase (TdT) enzyme or a truncated version thereof or the homologous amino acid sequence of a terminal deoxynucleotidyl transferase (TdT) enzyme in other species or the homologous amino acid sequence of Polμ, Polβ, Polλ and Polθ of any species or the homologous amino acid sequence of X family polymerases of any species.

The synthesis may be performed in a microfluidic device, for example an electrowetting-on-dielectric (EWOD) device. Alternatively the synthesis may be performed in a microtitre plate format.

BRIEF DESCRIPTION OF THE DRAWINGS

FIGS. 5-7 demonstrate real-time detection of protein expression. GFP1-10 detector polypeptide is present right from the start of the experiment. Fluorescent signal increases as GFP11 tags are expressed. These experiments were are performed in a base fluid comprising 0.2% Span 85 in dodecamethylpentasiloxane rather than Tween20 in aqueous and no surfactant in dodecane.

DETAILED DESCRIPTION OF THE INVENTION

Figure 1:
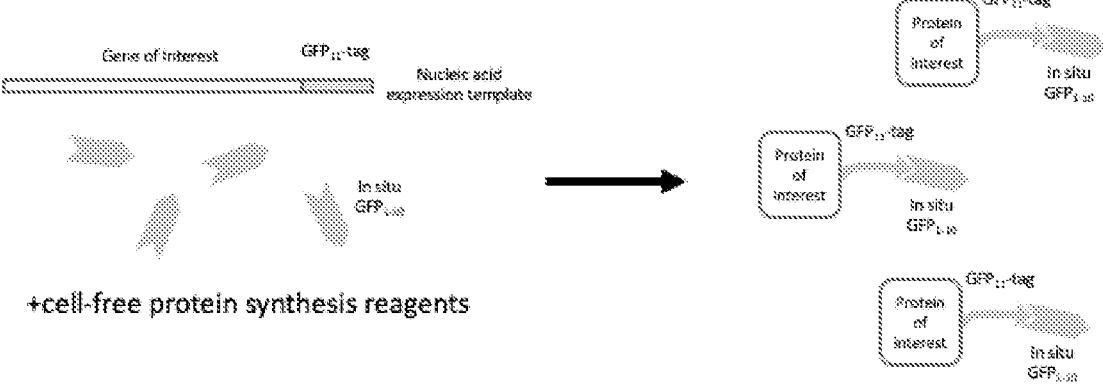
FIG. 1 shows schematically one embodiment of the invention. The cell-free protein synthesis reaction contains a nucleic acid template containing the expression cassette for the gene of interest fused to a detectable tag, which is then expressed into the protein of interest through coupled or uncoupled in vitro transcription and in vitro translation. The protein of interest is thus fused to a detectable peptide tag at the N- or C-termini. The nature of the detectable peptide tag is that it can be complemented with a complementary polypeptide resulting in a protein that is fluorescent.

Disclosed herein is a method for the real-time monitoring of in vitro protein synthesis comprising
 a. in vitro transcription and translation of a protein of interest fused to a peptide tag; and
 b. monitoring the presence of the peptide tag using a further polypeptide which in the presence of the peptide tag produces a detectable signal.
Disclosed herein is a method for the monitoring of cell free protein synthesis in a droplet on a digital microfluidic device comprising
 a. cell free transcription and translation of a protein of interest fused to a peptide tag; and
 b. monitoring the presence of the peptide tag using a further polypeptide which in the presence of the peptide tag produces a detectable signal.
Disclosed is a method for the cell-free expression of peptides or proteins in a digital microfluidic device. The droplets having the components required for cell-free protein synthesis (CFPS), otherwise known as in vitro protein synthesis, can be manipulated by electrokinesis in order to effect and improve protein expression.

Electrowetting is the modification of the wetting properties of a surface (which is typically hydrophobic) with an applied electric field. Microfluidic devices for manipulating droplets or magnetic beads based on electrowetting have been extensively described. In the case of droplets in channels this can be achieved by causing the droplets, for example in the presence of an immiscible carrier fluid, to travel through a microfluidic channel defined by the walls of a cartridge or microfluidic tubing. Embedded in the walls of the cartridge or tubing are electrodes covered with a dielectric layer each of which are connected to an A/C biasing circuit capable of being switched on and off rapidly at intervals to modify the electrowetting field characteristics of the layer. This gives rise to the ability to steer the droplet along a given path. As an alternative to microfluidic channel systems, droplets can also be generated and manipulated on planar surfaces using digital microfluidics (DMF). In contrast to channel based microfluidics, DMF utilizes alternating currents on an electrode array for moving fluid on the surface of the array. Liquids can thus be moved on an open-plan device by electrowetting. Digital microfluidics allows precise control over the droplet movements including droplet fusion and separation.

Cell-free protein synthesis, also known as in vitro protein synthesis or CFPS, is the production of peptides or proteins using biological machinery in a cell-free system, that is, without the use of living cells. The in vitro protein synthesis environment is not constrained within a cell wall or limited by conditions necessary to maintain cell viability, and enables the rapid production of any desired protein from a nucleic acid template, usually plasmid DNA or RNA from an in vitro transcription. CFPS has been known for decades, and many commercial systems are available. Cell-free protein synthesis encompasses systems based on crude lysate (*Cold Spring Harb Perspect Biol.* 2016 Dec; 8(12): a023853) and systems based on reconstituted, purified molecular reagents, such as the PURE system for protein production (*Methods Mol Biol.* 2014; 1118: 275-284). CFPS requires significant concentrations of biomacromolecules, including DNA, RNA, proteins, polysaccharides, molecular crowding agents, and more (*Febs Letters* 2013, 2, 58, 261-268).

To date, digital microfluidics, electrowetting-on-dielectric (EWoD), and electrokinesis in general have only found limited uses in cell-free biological-based applications, mostly due to biofouling, where biological components such as proteins, nucleic acids, crude cell extracts and other bioproducts adsorb and/or denature to hydrophobic surfaces. Biofouling is well known in the art to limit the ability of EWoD devices to manipulate droplets containing biomacromolecules. Wheeler and colleagues report that the maximum actuation time for droplets on EWoD devices containing biological media is 30 min before biofouling inhibits EWoD-based droplet actuation (*Langmuir* 2011, 27, 13, 8586-8594).

Digital microfluidics can be carried out in an air-filled system where the liquid drops are manipulated on the surface in air. However, at elevated temperatures or over prolonged periods, the volatile aqueous droplets simply dry onto the surface by evaporation. This issue is compounded by the high surface area to volume ratio of nanoliter and microliter sized drops. Hence air-filled systems are generally not suitable for protein expression where the temperature of the system needs to be maintained at a temperature suitable for enzyme activity and the duration of the synthesis needs to be prolonged for synthesized proteins levels to be detectable.

Protein expression typically requires an ample supply of oxygen. The most convenient and high yielding way to power CFPS is via oxidative phosphorylation where $O_2$ serves as the final electron acceptor; however, there are other ways that involve replenishing with energy molecules not involved in oxidative phosphorylation. In a confined microfluidic or digital microfluidic system of droplets, insufficient oxygen is available to enable efficient protein synthesis.

Described herein are improved methods allowing for the cell-free expression of peptides or proteins in a digital microfluidic device. Included is a method for the cell-free expression of peptides or proteins in a microfluidic device wherein the method comprises one or more droplets containing a nucleic acid template (i.e., DNA or RNA) and a cell-free system having components for protein expression in an oil-filled environment, and moving said droplets using electrokinesis. The components for the cell-free protein synthesis droplet can be pre-mixed prior to introduction to or mixed on the digital microfluidic device.

The droplet can be repeatedly moved for at least a period of 30 minutes whilst the protein is expressed. The droplet can be repeatedly moved for at least a period of two hours whilst the protein is expressed. The droplet can be repeatedly moved for at least a period of twelve hours whilst the protein is expressed. The act of moving the droplet allows oxygen to be supplied to the droplet and dispersed throughout the droplet. The act of moving improves the level of protein expression over a droplet which remains static.

The droplet can be moved using any means of electrokinesis. The droplet can be moved using electrowetting-on-dielectric (EWoD). The electrical signal on the EWoD or optical EWoD device can be delivered through segmented electrodes, active-matrix thin-film transistors, or digital micromirrors.

The oil in the device can be any water immiscible liquid. The oil can be mineral oil, silicone oil, an alkyl-based solvent such as decane or dodecane, or a fluorinated oil. The oil can be oxygenated prior to or during the expression process. Alternatively, the device can be an air-filled device where droplets containing cell-free protein synthesis reagents are rapidly moved into position and fixed into an array under a humidified gas to prevent evaporation. Humidification can be achieved by enclosing or sealing the digital microfluidic device and providing on-board reagent reservoirs. Additionally, humidification can be achieved by connecting an aqueous reservoir to an enclosed or sealed digital microfluidic device. The aqueous reservoir can have a defined temperature or solute concentration in order to provide specific relative humidities (e.g., a saturated potassium sulfate solution at 30° C.).

A source of supplemental oxygen can be supplied to the droplets. For example droplets or gas bubbles containing gaseous or dissolved oxygen can be merged with the droplets during the protein expression. Additionally, a source of supplemental oxygen can be found by oxygenating the oil that is used as the filler medium. It is well-known in the art that oils such as hexadecane, HFE-7500, and others can be oxygenated to support the oxygen requirements of cell growth, especially *E. coli* cell growth (*RSC Adv.*, 2017, 7, 40990-40995). Oxygenation can be achieved by aerating the oil with pure oxygen or atmospheric air.

The droplets can be formed before entering the microfluidic device and flowed into the device. Alternatively the droplets can be merged on the device. Included is a method comprising merging a first droplet containing a nucleic acid template such as a plasmid with a second droplet containing a cell-free extract having the components for protein expression to form a combined droplet capable of cell-free protein synthesis.

The droplets can be split on the device either before or after expression. Included herein is a method further comprising splitting the aqueous droplet into multiple droplets. If desired the split droplets can be screened with further additives. Included is a method wherein one or more of the split droplets are merged with additive droplets for screening.

The cell-free expression of peptides or proteins can use a cell lysate having the reagents to enable protein expression. Common components of a cell-free reaction include an energy source, a supply of amino acids, cofactors such as magnesium, and the relevant enzymes. A cell extract is obtained by lysing the cell of interest and removing the cell walls, DNA genome, and other debris by centrifugation. The remains are the cell machinery including ribosomes, aminoacyl-tRNA synthetases, translation initiation and elongation factors, nucleases, etc. Once a suitable nucleic acid template is added, the nucleic acid template can be expressed as a peptide or protein using the cell derived expression machinery.

Any particular nucleic acid template can be expressed using the system described herein. Three types of nucleic acid templates used in CFPS include plasmids, linear expression templates (LETs), and mRNA. Plasmids are circular templates, which can be produced either in cells or synthetically. LETs can be made via PCR. While LETs are easier and faster to make, plasmid yields are usually higher in CFPS. mRNA can be produced through in vitro transcription systems. The methods use a single nucleic acid template per droplet. The methods can use multiple droplets having a different nucleic acid template per droplet.

An energy source is an important part of a cell-free reaction. Usually, a separate mixture containing the needed energy source, along with a supply of amino acids, is added to the extract for the reaction. Common sources are phosphoenolpyruvate, acetyl phosphate, and creatine phosphate.

The energy source can be replenished during the expression process by adding further reagents to the droplet during the process.

The cell-free extract having the components for protein expression includes everything required for protein expression apart from the nucleic acid template. Thus the term includes all the relevant ribosomes, enzymes, initiation factors, nucleotide monomers, amino acid monomers, metal ions and energy sources. Once the nucleic acid template is added, protein expression is initiated without further reagents being required.

Thus the cell-lysate can be supplemented with additional reagents prior to the template being added. The cell-free extract having the components for protein expression would typically be produced as a bulk reagent or 'master mix' which can be formulated into many identical droplets prior to the distinct template being separately added to separate droplets. Common cell extracts in use today are made from *E. coli* (ECE), rabbit reticulocytes (RRL), wheat germ (WGE), insect cells (ICE) and Yeast *Kluyveromyces* (the D2P system). All of these extracts are commercially available.

Rather than originating from a cell extract, the cell-free system can be assembled from the required reagents. Systems based on reconstituted, purified molecular reagents are commercially available, for example the PURE system for protein production, and can be used as supplied. The PURE system is composed of all the enzymes that are involved in transcription and translation, as well as highly purified 70S ribosomes. The protein synthesis reaction of the PURE system lacks proteases and ribonucleases, which are often present as undesired molecules in cell extracts.

The term digital microfluidic device refers to a device having a two-dimensional array of planar microelectrodes. The term excludes any devices simply having droplets in a flow of oil in a channel. The droplets are moved over the surface by electrokinetic forces by activation of particular electrodes. Upon activation of the electrodes the dielectric layer becomes less hydrophobic, thus causing the droplet to spread onto the surface. A digital microfluidic (DMF) device set-up is known in the art, and depends on the substrates used, the electrodes, the configuration of those electrodes, the use of a dielectric material, the thickness of that dielectric material, the hydrophobic layers, and the applied voltage.

Once the CFPS reagents have been enclosed in the droplets, additional reagents can be supplied by merging the original droplet with a second droplet. The second droplet can carry any desired additional reagents, including for example oxygen or 'power' sources, or test reagents to which it is desired to expose to the expressed protein.

The droplets can be aqueous droplets. The droplets can contain an oil immiscible organic solvent such as for example DMSO. The droplets can be a mixture of water and solvent, providing the droplets do not dissolve into the bulk oil.

The droplets can be in a bulk oil layer. A dry gaseous environment simply dries the bubbles onto the surface during the expression process, leaving comet type smears of dried material by evaporation. Thus the device is filled with liquid for the expression process. Alternatively, the aqueous droplets can be in a humidified gaseous environment. A device filled with air can be sealed and humidified in order to provide an environment that reduces evaporation of CFPS droplets.

The droplets containing the cell-free extract having the components for protein expression will therefore typically be in the oil filled environment before the nucleic acid templates are added to the droplets. The templates can be added by merging droplets on the microfluidic device. Alternatively, the templates can be added to the droplets outside the device and then flowed into the device for the expression process. For example the expression process can be initiated on the device by increasing the temperature. The expression system typically operates optimally at temperatures above standard room temperatures, for example at or above 29° C.

The expression process typically takes many hours. Thus the process should be left for at least minutes or 1 hour, typically at least 2 hours. Expression can be left for at least 12 hours. During the process of expression the droplets should be moved within the device. The moving improves the process by mixing the reagents and ensuring sufficient oxygen is available within the droplet. The moving can be continuous, or can be repeated with intervening periods of non-movement.

Thus the aqueous droplet can be repeatedly moved for at least a period of 30 minutes or one hour whilst the protein is expressed. The aqueous droplet can be repeatedly moved for at least a period of two hours whilst the protein is expressed. The aqueous droplet can be repeatedly moved for at least a period of twelve hours whilst the protein is expressed. The act of moving the droplet allows mixing within the droplet, and allows oxygen or other reagents to be supplied to the droplet. The act of moving improves the level of protein expression over a droplet which remains static.

Digital microfluidics (DMF) refers to a two-dimensional planar surface platform for lab-on-a-chip systems that is based upon the manipulation of microdroplets. Droplets can be dispensed, moved, stored, mixed, reacted, or analyzed on a platform with a set of insulated electrodes. Digital microfluidics can be used together with analytical analysis procedures such as mass spectrometry, colorimetry, electrochemical, and electrochemiluminescence.

The droplet can be moved using any means of electrokinesis. The aqueous droplet can be moved using electrowetting-on-dielectric (EWoD). Electrowetting on a dielectric (EWOD) is a variant of the electrowetting phenomenon that is based on dielectric materials. During EWoD, a droplet of a conducting liquid is placed on a dielectric layer with insulating and hydrophobic properties. Upon activation of the electrodes the dielectric layer becomes less hydrophobic, thus causing the droplet to spread onto the surface.

The electrical signal on the EWoD or optically-activated amorphous silicon (a-Si) EWoD device can be delivered through segmented electrodes, active-matrix thin-film transistors or digital micromirrors. Optically-activated s-Si EWoD devices are well known in the art for actuating droplets (*J. Adhes. Sci. Technol.*, 2012, 26, 1747-1771).

The oil in the device can be any water immiscible or hydrophobic liquid. The oil can be mineral oil, silicone oil, an alkyl-based solvent such as decane or dodecane, or a fluorinated oil. The air in the device can be any humidified gas.

A source of supplemental oxygen can be supplied to the droplets. For example droplets or gas bubbles containing gaseous or dissolved oxygen can be merged with the aqueous droplets during the protein expression. Alternatively the source of oxygen can be a molecular source which releases oxygen. Alternatively the droplets can be moved to an air/liquid boundary to enable increased diffusion of oxygen from a gaseous environment. Alternatively the oil can be oxygenated. Alternatively the droplets can be presented in a humidified air filled device.

The droplet can be formed before entering the microfluidic device and flowed into the device. Alternatively the droplets can be merged on the device. Included is a method comprising merging a first droplet containing a nucleic acid template such as a plasmid with a second droplet containing a cell-free system having the components for protein expression to form the droplet.

The droplets can be split on the device either before, during or after expression. Included herein is a method further comprising splitting the droplet into multiple droplets. If desired the split droplets can be screened with further additives. Included is a method wherein one of more of the split droplets are merged with additive droplets for screening.

Through an affinity tag, such as a FLAG-tag, HIS-tag, GST-tag, MBP-tag, STREP-tag, or other form of affinity tag, CFPS-expressed proteins can be immobilized to a solid-support affinity resin and fresh batches of CFPS reagent can be delivered over the said resin. Thus, renewed reagents can be used to carry out protein synthesis, closely mimicking industrial methods of continuous flow (CF) and continuous exchange (CE) CFPS. By mimicking CF- and CE-CFPS, users can scale up their CFPS production methods.

The droplets can be actuated on a hydrophobic surface on the digital microfluidic device (ACS Nano 2018, 12, 6, 6050-6058). The hydrophobic surface can be a hydrophobic surface such as polytetrafluoroethylene (PTFE), Teflon AF (DuPont Inc), CYTOP (AGC Chemicals Inc), or FluoroPel (Cytonix LLC). The hydrophobic surface may be modified in such a way to reduce biofouling, especially biofouling resulting from exposure to CFPS reagents or nucleic acid reagents. The hydrophobic surface may also be superhydrophobic, such as NeverWet (NeverWet LLC) or Ultra-Ever Dry (Flotech Performance Systems Ltd). Superhydrophobic surfaces prevent biofouling compared with typical fluorocarbon-based hydrophobic surfaces. Superhydrophobic surfaces thus prolong the capability of digital microfluidic devices to move CFPS droplets and general solutions containing biopolymers (RSC Adv., 2017, 7, 49633-49648). The hydrophobic surface can also be a slippery liquid infused porous surface (SLIPS), which can be formed by infusing Krtox-103 oil (DuPont) with porous PTFE film (Lab Chip, 2019, 19, 2275).

Droplets can also contain additives to reduce the effects of biofouling on digital microfluidic surfaces. Specifically, droplets containing CFPS components can also contain additives such as surfactants or detergents to reduce the effects of biofouling on the hydrophobic or superhydrophobic surface of a digital microfluidic device (Langmuir 2011, 27, 13, 8586-8594). Such droplets may use antifouling additives such as TWEEN 20, Triton X-100, and/or Pluronic F127. Specifically, droplets containing CFPS components may contain TWEEN 20 at 0.1% v/v, Triton X-100 at 0.1% v/v, and/or Pluronic F127 at 0.08% w/v.

Figure 8:
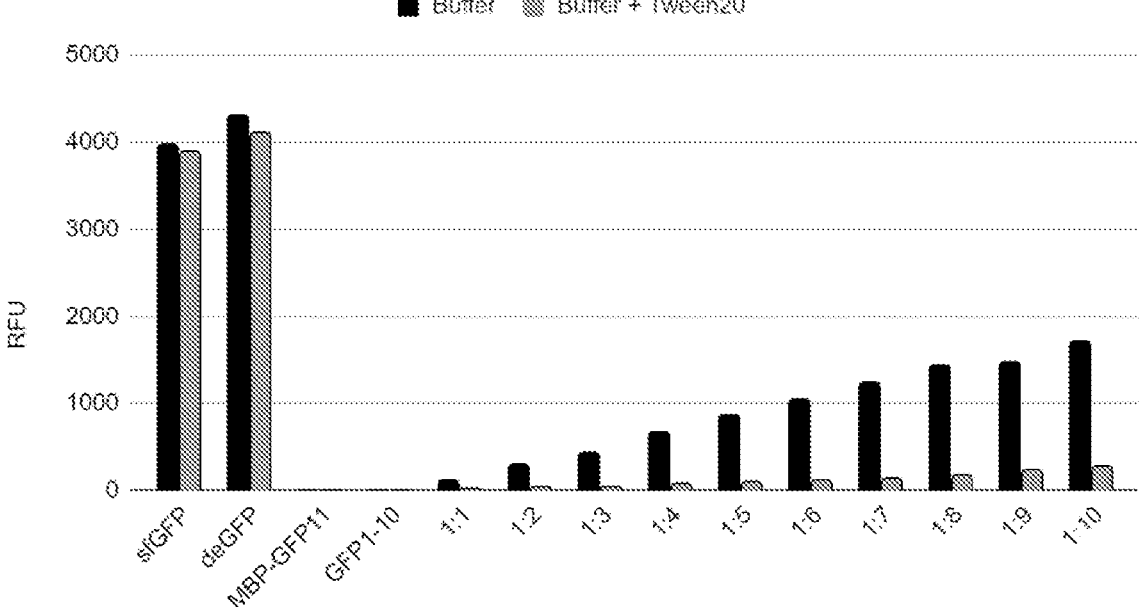
FIG. 8 Demonstration that the complementation of the GFP11 tag with recombinant GFP1-10 detector is inhibited in the presence of 0.1% w/v Tween20 surfactant. The complementation assay was performed in TNG Buffer (50 mM Tris, pH 7.4, 0.1 M NaCl, 10% v/v glycerol). Fluorescence was measured after 24 hours incubation at 29° C. The first four pairs are controls: sfGFP and deGFP are complete fluorescent proteins, while MBP-GFP11 and GFP1-10 are partial fluorescent proteins (tag and detector respectively) hence show no fluorescence. The ten sample pairs have the same quantity of MBP-GFP11 but increasing molar excesses of recombinant GFP1-10 detector polypeptide. The data also shows that increasing the molar excess of GFP1-10 detector polypeptide over the GFP11 peptide tag leads to enhanced fluorescence signal.
Figure 9:
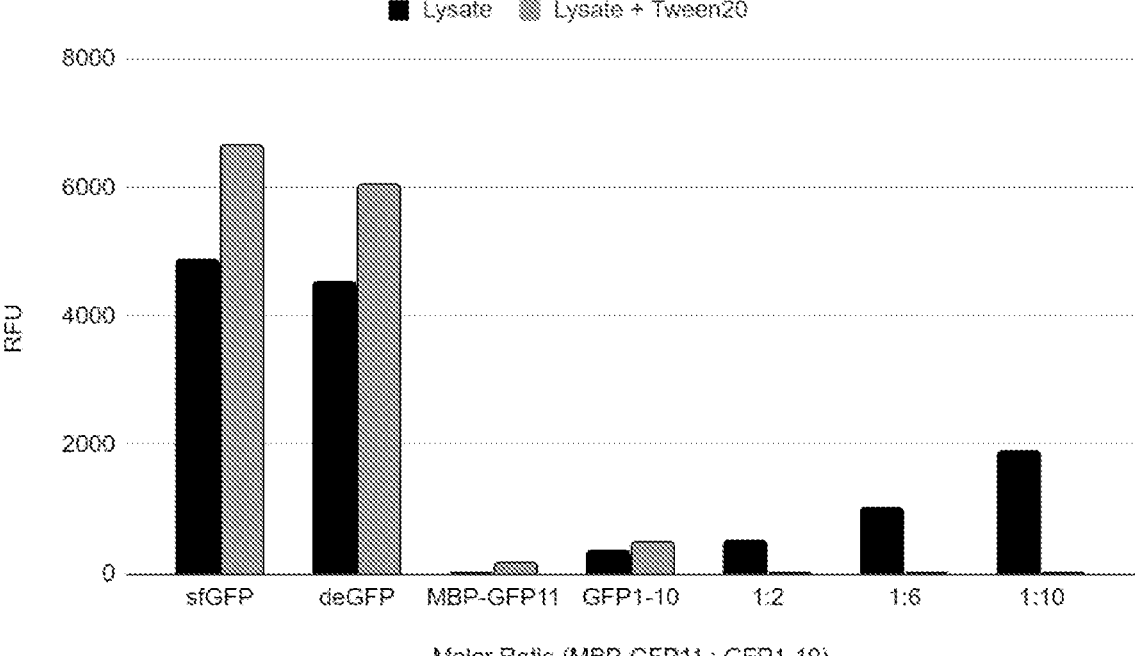
FIG. 9 Demonstration that the complementation of the GFP11 tag with recombinant GFP1-detector is inhibited in the presence of 0.1% w/v Tween20 surfactant. The complementation assay was performed in a cell-free lysate (σ70 Linear Master Mix, Arbor Bioscience). Fluorescence was measured after 24 hours incubation using a plate reader. The first four pairs are controls: sfGFP and deGFP are complete fluorescent proteins, while MBP-GFP11 and GFP1-10 are partial fluorescent proteins (tag and detector respectively) hence show no fluorescence. The three sample pairs have the same quantity of MBP-GFP11 but increasing molar excesses of recombinant GFP1-10 detector polypeptide.

For electrowetting on dielectrics (EWoD), the change in contact angle of reagent upon the application of electric potential is an inverse function of surface tension. Thus, for low voltage EWOD operations, reduction in surface tension is achieved by addition of surfactants to reagents, which for CFPS reactions means to the lysate and to the DNA. This results in a dilution of the lysate, and it has been seen, in experiments, that diluting or otherwise adulterating the lysate results in a decrease in expression level of the protein of interest. Thus performing CFPS on DMF where the surfactants are added to the solutions being moved will necessarily result in a dilution and adulteration of the lysate and thus a decrease in the level of protein expression. In addition to being a problem in its own right, this further complicates extrapolation of on-DMF results to in-tube predictions of protein yield. An additional detriment of having to add surfactants to the samples is that this increases the time required for sample preparation, as well as increasing the potential for inconsistent results due to 'user error,' as there is more handling of reagents. An additional detriment of having to add surfactants to the samples is that certain downstream operations are hindered. For example, if a protein of interest is expressed in a cell free system with a GFP 11 (or similar) peptide tag, it's downstream complementation with a GFP1-10 (or similar) detector polypeptide is hindered in the presence of surfactant. This is shown in FIGS. 8 and 9. Removal of the surfactant from the aqueous phase is therefore advantageous.

Rather than adding surfactants to the aqueous sample, it is instead possible to add surfactant, such as a sorbitan ester such as Span85 (e.g. Sorbitan trioleate, Sigma Aldrich, SKU 8401240025), to the oil. This has the advantages of enabling CFPS reactions to proceed on-DMF without dilution or adulteration. Additionally, it simplifies the sample preparation procedure for setting up the reactions, increasing the ease of use and the consistency of results. Using 1% w/w Span85 in dodecane allows for dilution-free CFPS reactions on-DMF, as well as dilution-free detection of the expressed non-fluorescent proteins. Other surfactants besides Span85, and oils other than dodecane could be used. A range of concentrations of Span85 could be used. Surfactants could be nonionic, anionic, cationic, amphoteric or a mixture thereof. Oils could be mineral oils or synthetic oils, including silicone oils, petroleum oils, and perfluorinated oils. Surfactants can have a detrimental effect on (1) the CFPS reactions and (2) the efficiency of the detection system (if the detection system involves complementation of a tag and detector). For example, by performing the CFPS reaction on-DMF with oil-surfactant mix, the detection of the expressed protein can also proceed without dilution and without adding aqueous surfactant. It has been shown that surfactants reduce the efficiency of some detection systems, including but not limited to the Split GFP (e.g. GFP11/ GFP1-10) system, so removing surfactants from the reagent mix and instead adding them to the oil can be beneficial.

The peptide tag can be attached to the C or N terminus of the protein. The peptide tag may be one component of a green fluorescent protein (GFP). For example the peptide tag may be $GFP_{11}$ and the further polypeptide $GFP_{1-10}$. The peptide tag may be one component of sfCherry. The peptide tag may be $sfCherry_{11}$ and the further polypeptide $sfCherry_{1-10}$.

The protein may be fused to multiple tags. For example the protein may be fused to multiple $GFP_{11}$ peptide tags and the synthesis occurs in the presence of multiple $GFP_{1-10}$ polypeptides. For example the protein may be fused to multiple $sfCherry_{11}$ peptide tags and the synthesis occurs in the presence of multiple $sfCherry_{1-10}$ polypeptides. The protein of interest may be fused to one or more $sfCherry_{11}$ peptide tags and one or more $GFP_{11}$ peptide tags and the synthesis occurs in the presence of one or more $GFP_{1-10}$ polypeptides and one or more $sfCherry_{1-10}$ polypeptides.

Devices

The manipulation of droplets by the application of electrical potential can be achieved on electrodes covered with an insulator or a dielectric or a series of insulators or dielectrics. Droplet manipulation as a result of an applied electrical potential is known as electrowetting. Electrokinesis occurs as result of a non-uniform electric field that influences the hydrostatic equilibrium of a dielectric liquid (dielectrophoresis or DEP) or a change in the contact angle of the liquid on solid surface (electrowetting-on-dielectric or EWoD). DEP can also be used to create forces on polarizable particles to induce their movement. The electrical signal can be transmitted to a discrete electrode, a transistor, an array of transistors, or a sheet of semi-conductor film whose electrical properties can be modulated by an optical signal.

EWoD phenomena occur when droplets are actuated between two parallel electrodes covered with a hydrophobic insulator or dielectric. The electric field at the electrode-electrolyte interface induces a change in the surface tension, which results in droplet motion as a result of a change in droplet contact angle. The electrowetting effect can be quantitatively treated using Young-Lippmann equation:

$$\cos\theta - \cos\theta_0 = (\tfrac{1}{2}\gamma LG)c \cdot V^2$$

where $\theta_0$ is the contact angle when the electric field across the interfacial layer is zero, $\gamma LG$ is the liquid-gas tension, c is the specific capacitance (given as $\varepsilon_r \cdot \varepsilon_0/t$, where $\varepsilon_r$ is dielectric constant of the insulator/dielectric, $\varepsilon_0$ is permittivity of vacuum, t is thickness) and V is the applied voltage or electrical potential. The change in contact angle (inducing droplet movement) is thus a function of surface tension, electrical potential, dielectric thickness, and dielectric constant.

When a droplet is actuated by EWoD, there are two opposing sets of forces that act upon it: an electrowetting force induced by electric field and resistant forces that include the drag forces resulting from the interaction of the droplet with filler medium and the contact line friction (ref). The minimum voltage applied to balance the electrowetting force with the sum of all drag forces (threshold voltage) is variably determined by the thickness-to-dielectric contact ratio of the insulator/dielectric, $(t/\varepsilon_r)^{1/2}$. Thus, to reduce actuation voltage, it is required to reduce $(t/\varepsilon_r)^{1/2}$ (i.e., increase dielectric constant or decrease insulator/dielectric thickness). To achieve low voltage actuation, thin insulator/ dielectric layers must be used. However, the deposition of high quality thin insulator/dielectric layers is a technical challenge, and these thin layers are easily damaged before the desired electrowetting contact angle is large enough to drive the droplet is achieved. Most academic studies thus report the use of much higher voltages >100V on easily fabricated, thick dielectric films (>3 μm) to effect electrowetting.

High voltage EWoD-based devices with thick dielectric films, however, have limited industrial applicability largely due to their limited droplet multiplexing capability. The use of low voltage devices including thin-film transistors (TFT) and optically-activated amorphous silicon layers (a-Si) have paved the way for the industrial adoption of EWoD-based devices due to their greater flexibility in addressing electrical signals in a highly multiplex fashion. The driving voltage for TFTs or optically-activated a-Si are low (typically <15 V). The bottleneck for fabrication and thus adoption of low voltage devices has been the technical challenge of depositing high quality, thin film insulators/dielectrics. Hence there has been a particular need for improving the fabrication and composition of thin film insulator/dielectric devices.

Typically, the electrodes (or the array elements) used for EWoD are covered with (i) a hydrophilic insulator/dielectric and a hydrophobic coating or (ii) a hydrophobic insulator/ dielectric. Commonly used hydrophobic coatings comprise of fluoropolymers such as Teflon AF 1600 or CYTOP. The thickness of this material as a hydrophobic coating on the dielectric is typically <100 nm and can have defects in the form of pinholes or a porous structure; hence, it is particularly important that the insulator/dielectric is pinhole free to avoid electrical shorting. Teflon has also been used as an insulator/dielectric, but it has higher voltage requirements due to its low dielectric constant and the thickness required to make it pinhole free. Other hydrophobic insulator/dielectric materials can include polymer-based dielectrics such as those based on siloxane, epoxy (e.g. SU-8), or parylene (e.g., parylene N, parylene C, parylene D, or parylene HT). Due to minimal contact angle hysteresis and a higher contact angle with aqueous solutions, Teflon is still used as a hydrophobic topcoat on these insulator/dielectric polymers. However, there are difficulties in reliably producing <1 micron pinhole-free coatings of parylene or SU-8; thus, the thickness of these materials is typically kept at a 2-5 microns at the cost of increased voltage requirements for electrowetting. It has also been reported that traditional EWoD devices with parylene C are easily broken and unstable for repeated droplet manipulation with cell culture medium. Multi-layer insulator devices deposited with metal-oxide and parylene C films have been used to produce a more robust insulator/dielectric and enable operations with lower applied voltages. Inorganic materials, such metal oxides and semiconductor oxides, commonly used in the CMOS industry as "gate dielectrics", have been used as insulator/dielectric for EWoD devices. They offer the advantage of utilizing standard cleanroom processes for thin film depositions (<100 nm). These materials are inherently hydrophilic, requiring an additional hydrophobic coating, and can be prone to pinhole formation as a result of thin film layer deposition process. Together with the need for lower voltage operations of EWoD, recent developmental work has focused on (1) using materials with improved dielectric properties (e.g., using high-dielectric constant insulators/dielectrics), (2) optimizing the fabrication process to make the insulator/dielectric pinhole free to avoid dielectric breakdown.

Operation of EWoD devices suffers from contact angle saturation and hysteresis, which is believed to be brought about by either one or combination of these phenomena: (1) entrapment of charges in the hydrophobic film or insulator/dielectric interface, (2) adsorption of ions, (3) thermodynamic contact angle instabilities, (4) dielectric breakdown of dielectric layer, (5) the electrode-electrode-insulator interface capacitance (arising from the double layer effect), and (6) fouling of the surface (such as by biomacromolecules). One of the adverse effects of this hysteresis is reduced operational lifetime of the EWoD-based device.

Contact angle hysteresis is believed to be a result of charge accumulation at the interface or within the hydrophobic insulator after several operations. The required actuation voltage increases due to this charging phenomenon resulting in eventual catastrophic dielectric breakdown. The most probable explanation is that pinholes at the insulator/dielectric may allow the liquid to come into contact with the electrode causing electrolysis. Electrolysis is further facilitated by pinhole-prone or porous hydrophobic insulators.

Most of the studies to understand contact angle hysteresis on EWoD have been conducted on short time scales and with low conductivity solutions. Long duration actuations (e.g., >1 hour) and high conductivity solutions (e.g., 1 M NaCl) could produce several effects other than electrolysis. The ions in solution can permeate through the hydrophobic coat (under the applied electric field) and interact with the underlying insulator/dielectric. Ion permeation can result in (1) change in dielectric constant due to charge entrapment (which is different from interfacial charging) and (2) change in surface potential of a pH sensitive metal oxide. Both can result in reduction of electrowetting forces to manipulate aqueous droplets, leading to contact angle hysteresis. The inventors have previously found that the damage from high conductivity solutions reduces or disables electrowetting on electrodes by inhibiting the modulation of contact angle when an electric field is applied.

An electrokinetic device includes a first substrate having a matrix of electrodes, wherein each of the matrix electrodes is coupled to a thin film transistor, and wherein the matrix electrodes are overcoated with a functional coating comprising: a dielectric layer in contact with the matrix electrodes, a conformal layer in contact with the dielectric layer, and a hydrophobic layer in contact with the conformal layer; a second substrate comprising a top electrode; a spacer disposed between the first substrate and the second substrate and defining an electrokinetic workspace; and a voltage source operatively coupled to the matrix electrodes.

The dielectric layer may comprise silicon dioxide, silicon oxynitride, silicon nitride, hafnium oxide, yttrium oxide, lanthanum oxide, titanium dioxide, aluminum oxide, tantalum oxide, hafnium silicate, zirconium oxide, zirconium silicate, barium titanate, lead zirconate titanate, strontium titanate, or barium strontium titanate. The dielectric layer may be between 10 nm and 100 μm thick. Combinations of more than one material may be used, and the dielectric layer may comprise more than one sublayer that may be of different materials.

The conformal layer may comprise a parylene, a siloxane, or an epoxy. It may be a thin protective parylene coating in between the insulating dielectric and the hydrophobic coating. Typically, parylene is used as a dielectric layer on simple devices. In this invention, the rationale for deposition of parylene is not to improve insulation/dielectric properties such as reduction in pinholes, but rather to act as a conformal layer between the dielectric and hydrophobic layers. The inventors find that parylene, as opposed to other similar insulating coatings of the same thickness such as PDMS (polydimethylsiloxane), prevent contact angle hysteresis caused by high conductivity solutions or solutions deviating from neutral pH for extended hours. The conformal layer may be between 10 nm and 100 μm thick.

The hydrophobic layer may comprise a fluoropolymer coating, fluorinated silane coating, manganese oxide polystyrene nanocomposite, zinc oxide polystyrene nanocomposite, precipitated calcium carbonate, carbon nanotube structure, silica nanocoating, or slippery liquid-infused porous coating.

The elements may comprise one or more of a plurality of array elements, each element containing an element circuit; discrete electrodes; a thin film semiconductor in which the electrical properties can be modulated by incident light; and a thin film photoconductor whose properties can be modulated by incident light.

The functional coating may include a dielectric layer comprising silicon nitride, a conformal layer comprising parylene, and a hydrophobic layer comprising an amorphous fluoropolymer. This has been found to be a particularly advantageous combination.

The electrokinetic device may include a controller to regulate a voltage provided to the individual matrix electrodes. The electrokinetic device may include a plurality of scan lines and a plurality of gate lines, wherein each of the thin film transistors is coupled to a scan line and a gate line, and the plurality of gate lines are operatively connected to the controller. This allows all the individual elements to be individually controlled.

The second substrate may also comprise a second hydrophobic layer disposed on the second electrode. The first and second substrates may be disposed so that the hydrophobic layer and the second hydrophobic layer face each other, thereby defining the electrokinetic workspace between the hydrophobic layers.

The method is particularly suitable for aqueous droplets with a volume of 1 μL or smaller.

The EWoD-based devices shown and described below are active matrix thin film transistor devices containing a thin film dielectric coating with a Teflon hydrophobic top coat. These devices are based on devices described in the E Ink Corp patent filing on "Digital microfluidic devices including dual substrate with thin-film transistors and capacitive sensing", US patent application no 2019/0111433, incorporated herein by reference.

Described herein are electrokinetic devices, including:
a first substrate having a matrix of electrodes, wherein each of the matrix electrodes is coupled to a thin film transistor, and wherein the matrix electrodes are overcoated with a functional coating comprising:
a dielectric layer in contact with the matrix electrodes,
a conformal layer in contact with the dielectric layer, and
a hydrophobic layer in contact with the conformal layer;
a second substrate comprising a top electrode;
a spacer disposed between the first substrate and the second substrate and defining an electrokinetic workspace; and
a voltage source operatively coupled to the matrix electrodes;
Described herein is an electrokinetic device, including:
a first substrate having a matrix of electrodes, wherein each of the matrix electrodes is coupled to a thin film transistor, and wherein the matrix electrodes are overcoated with a functional coating comprising:
one or more dielectric layer(s) comprising silicon nitride, hafnium oxide or aluminum oxide in contact with the matrix electrodes,
a conformal layer comprising parylene in contact with the dielectric layer, and
a hydrophobic layer in contact with the conformal layer;
a second substrate comprising a top electrode;
a spacer disposed between the first substrate and the second substrate and defining an electrokinetic workspace; and
a voltage source operatively coupled to the matrix electrodes;

The electrokinetic devices as described may be used with other elements, such as for example devices for heating and cooling the device or reagent cartridges for the introduction of reagents as needed.

EXAMPLE

Example 1

A cDNA sequence encoding for a GFP 11-terminal deoxynucleotidyl transferase (GFP11_TdT) fusion protein was created.

```
GFP₁₁-terminal deoxynucleotidyl transferase
(GFP11_TdT) fusion protein (SEQ ID NO: 1):
MKRDHMVLHEYVNAAGITGSGGSGGKFMHHHHHHMENLYFQGKISQYAC

QRKTTLNNYNHIFTDAFEILAENSEFKENEVSYVTFMRAASVLKSLPFT

IISMKDTEGIPCLGDKVKCIIEEIIEDGESSEVKAVLNDERYQSFKLFT

SVFGVGLKTSEKWFRMGFRSLSKIMSDKTLKFTKMQKAGFLYYEDLVSC
```

-continued

```
VTRAEAEAVGVLVKEAVWAFLPDAFVTMTGGFRRGKKIGHDVDFLITSP

GSAEDEEQLLPKVINLWEKKGLLLYYDLVESTFEKFKLPSRQVDTLDHF

QKCFLILKLHHQRVDSSKSNQQEGKTWKAIRVDLVMCPYENRAFALLGW

TGSRQFERDIRRYATHERKMMLDNHALYDKTKRVFLKAESEEEIFAHLG

LDYIEPWERNA
```

The GFP₁₁-terminal deoxynucleotidyl transferase (GFP11_TdT) fusion protein comprised a 376 aa engineered TdT linked via a 9 aa linker to a 15 aa N-terminal GFP₁₁ peptide tag.

The GFP11_TdT cDNA sequence was cloned into a p70a vector and added (2 μl, 30 nM) to MyTXTL Sigma70 CFPS Master Mix (10 μl; Arbor Biosciences) resulting in a 12 μl total reaction volume.

A GFP₁₋₁₀ solution (0.9 mg/ml; 364 mM urea) was subsequently added to the CFPS reaction at 0, 1, 2, 3, 4, 6, and 12 μl resulting in a final CFPS urea concentration of 0, 28, 51, 72, 90, 120, and 180 mM, respectively.

The reactions were then incubated in a 200 μl PCR tube at 29° C. Photographs were taken under 470 nm blue light illuminator using a 580 nm filter.

Figure 2:
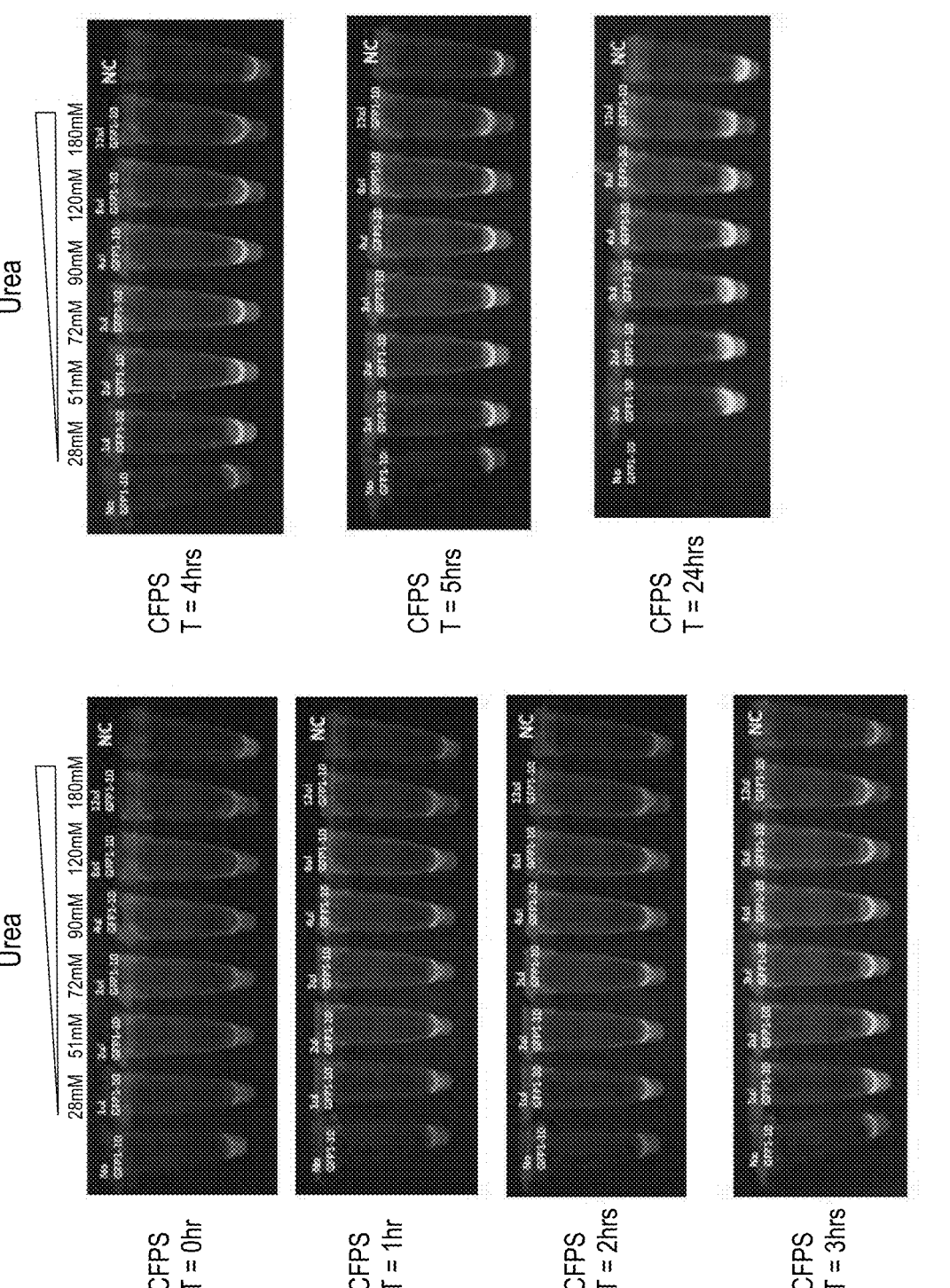
FIG. 2 shows real-time detection of the expression of a protein of interest in a cell-free protein synthesis reaction under blue light illumination. A GFP11_TdT was cloned into the p70a vector and added (2 μl, 30 nM) to MyTXTL Sigma70 CFPS Master Mix (10 μl; Arbor Biosciences) resulting in a 12 μl total reaction volume. A GFP$_{1-10}$ solution (0.9 mg/ml; 364 mM urea) was subsequently added to the CFPS reaction at 0, 1, 2, 3, 4, 6, and 12 μl resulting in a final CFPS urea concentration of 0, 28, 51, 72, 90, 120, and 180 mM, respectively. The reactions were then incubated in a 200 μl PCR tube at 29° C. Photographs were taken under 470 nm blue light illuminator using a 580 nm filter.

FIG. 2 shows the real-time fluorescent detection of GFP11_TdT in a CFPS reaction under blue light illumination. FIG. 2 optimises the amount of GFP₁₋₁₀ solution, which is a trade-off between increasing the concentration of the GFP₁₋₁₀ protein and CFPS inactivation through increasing concentrations of urea.

Figure 3:
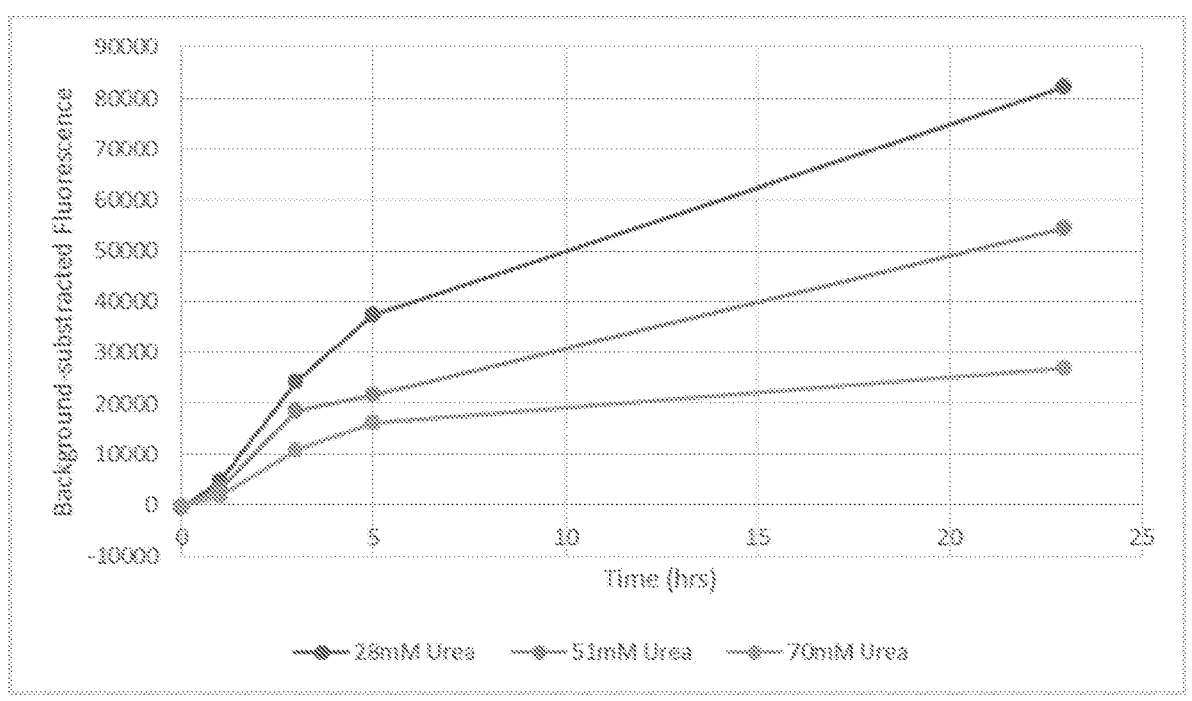
FIG. 3 shows graphically the real-time detection of the expression of a protein of interest in a cell-free protein synthesis reaction of FIG. 2. Fluorescence measurements were taken at indicated timepoints using an excitation wavelength of 485 nm and an emission wavelength of 520 nm. A negative control CFPS reaction containing GFP$_{1-10}$ solution but containing no GFP11_TdT p70a plasmid was used to subtract background fluorescence.

FIG. 3 quantifies the background subtracted, real-time fluorescent detection of GFP11_TdT in a CFPS reaction. Fluorescence measurements were taken at indicated timepoints using an excitation wavelength of 485 nm and an emission wavelength of 520 nm. A negative control CFPS reaction containing GFP₁₋₁₀ solution but containing no GFP11_TdT p70a plasmid was used to subtract background fluorescence.

Figure 4:
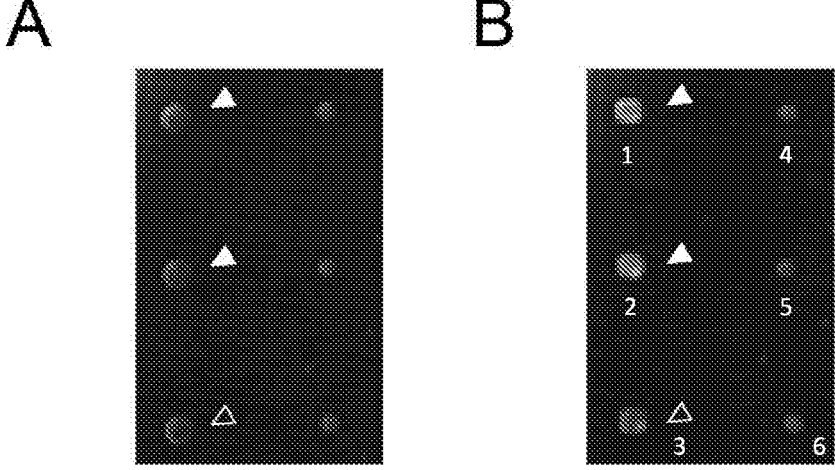
FIG. 4 shows (A) droplets on a digital microfluidic device containing cell-free protein synthesis lysate. The droplets annotated with a white arrow have been merged with recombinant GFP1-10 detector polypeptide (t=0). The top two rows additionally contain a DNA construct for the expression of a protein with a GFP11 peptide tag (solid white arrow). (B) Fluorescence image showing the same droplets as in panel (A) after six hours have elapsed. Only the droplets that contain both the expressed protein with GFP11 peptide tag and recombinant GFP-10 detector polypeptide (i.e. solid arrows) show a significant increase in fluorescence. Drops without DNA construct (hollow arrows) or with no GFP1-10 detector (no arrows) are not fluorescent. (C) Fluorescence quantification of drops in panel (B). Only the droplets with lysate, DNA construct, and GFP1-10 detector polypeptide show a significant increase in fluorescence, indicating protein expression. The negative controls, i.e. bottom row of drops in (B) contain no DNA construct and so low fluorescence, even in the presence of GFP1-10 detector. Numbering of drops in (B) and bars in (C) match.
Figure 4:
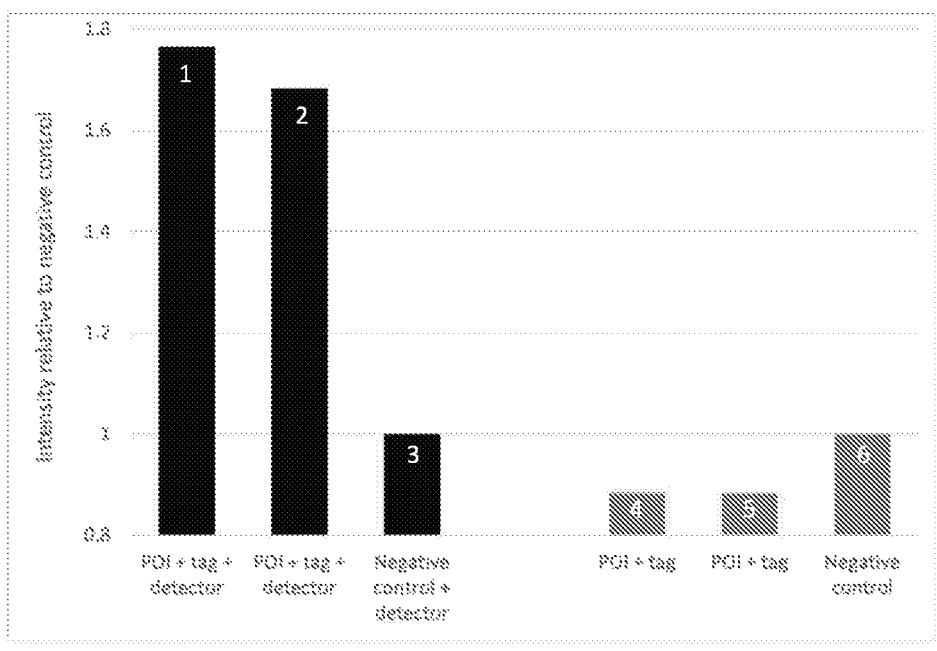

FIG. 4 shows measurements of expression in droplets on a microfluidic device. Droplets with tagged protein (maltose binding protein, MBP, fused to GFP11, i.e. MBP-GFP11) expressed in CFPS on eDrop can be seen in FIG. 4A. The first two rows contain CFPS lysate with protein expressed, while the third row contains a CPFS lysate control (no protein expressed). The image of FIG. 4A is taken under darkfield illumination.

Droplets where GFP1-10 has been added to some of the droplets with protein expressed, T=6 hours, shown in FIG. 4B. The larger droplets have had concentrated, recombinant GFP1-10 added to the CFPS lysate. This image is taken under fluorescent light. Only the droplets which have both the expressed tagged protein and the complementing polypeptide added show fluorescence.

Figure 5:
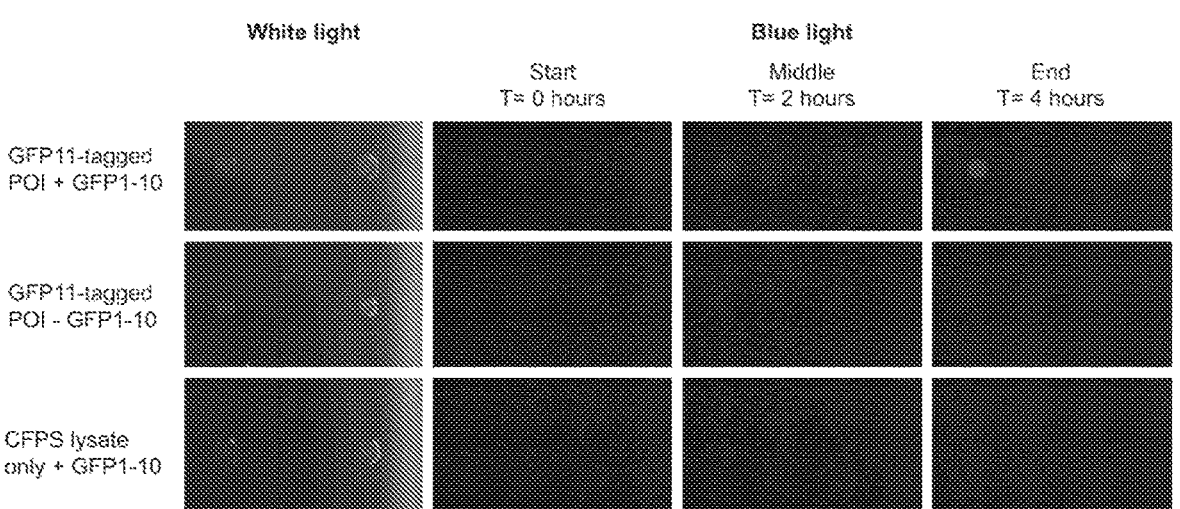
FIG. 5 Images extracted from a time course experiment whereby droplets of cell free protein synthesis (CFPS) lysate, optionally with a DNA construct for a protein of interest (POI—which here is maltose binding protein (MBP) tagged with a GFP11 peptide) and/or GFP1-10 polypeptide, were incubated on a digital microfluidic device for 4 hours and imaged periodically. Only the droplets containing lysate, DNA construct, and GFP1-10 polypeptide show a significant increase in fluorescence over the course of the experiment, as seen in the right-hand column of images.
Figure 6:
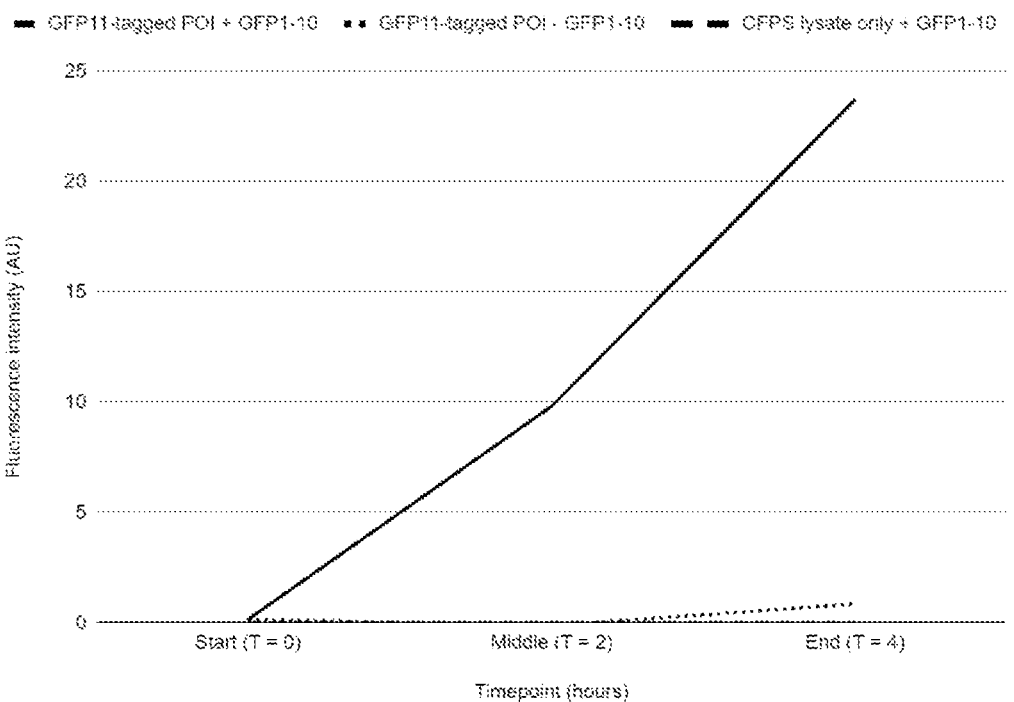
FIG. 6 A chart showing the real-time fluorescence increase seen in the droplets present in FIG. 5. Quantification of fluorescence was performed in Image J and the values presented have been subject to normalisation by subtracting the background fluorescence seen in droplets of CFPS lysate and GFP1-10 (i.e. no DNA construct so no protein of interest, POI, expressed). Only the droplets containing all components—lysate, DNA construct for POI, and GFP1-10 polypeptide—generate fluorescence over background.
Figure 7:
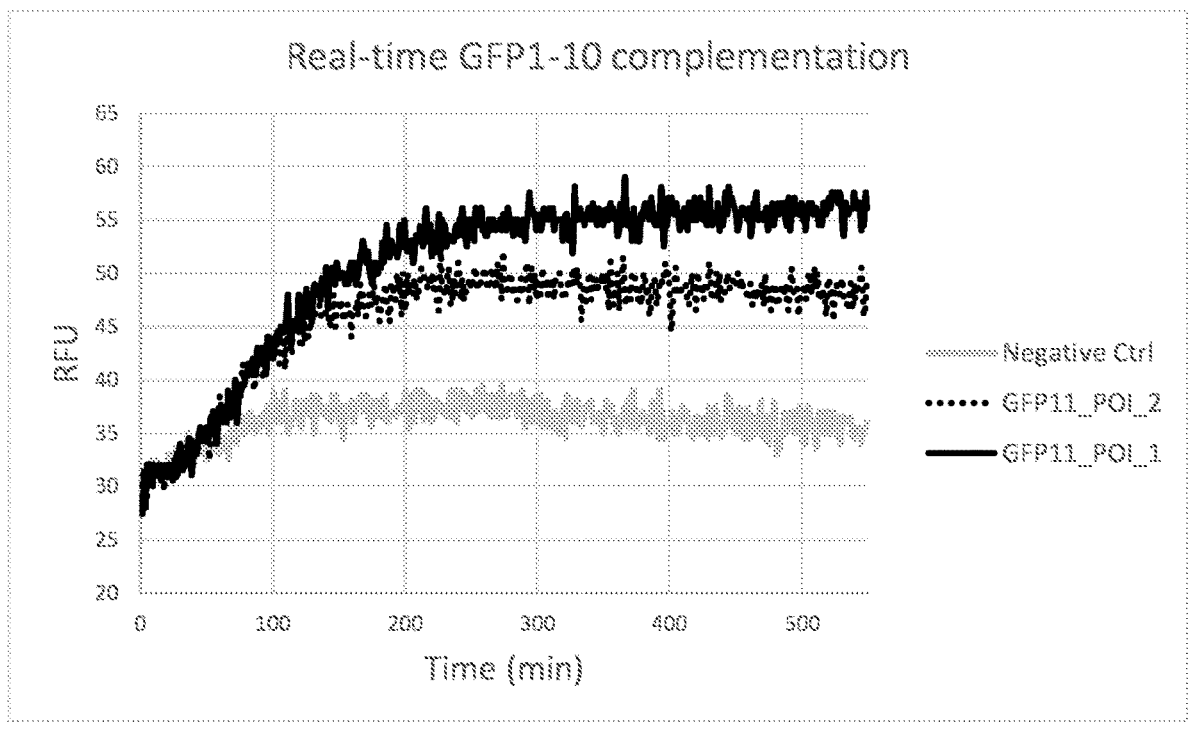
FIG. 7 In this experiment, the recombinantly purified GFP1-10 detector was added to the cell free lysate at the same time as the DNA construct encoding for a GFP11-tagged protein. The fluorescent signal was monitored over time in a plate reader. A chart showing fluorescence signal increases over time from plate reader measurements of CFPS reactions. GFP1-10 detector is present in all three reactions from the start, enabling real-time detection of protein expression. In the two conditions which have a protein of interest fused to a GFP11 tag, fluorescence increases compared to the negative control condition where there is no GFP11-tagged protein. POI1 is an engineered terminal transferase and POI2 is SARS-COV-NL63-Mpro. Both had a 3×GFP11 tag at the N terminus.

FIGS. 5-7 demonstrate real-time detection of protein expression. GFP1-10 detector polypeptide is present right from the start of the experiment. Fluorescent signal increases as GFP11 tags are expressed. These experiments were performed in a base fluid comprising 0.2% Span 85 in dodecamethylpentasiloxane rather than Tween20 in aqueous and no surfactant in dodecane.

FIGS. 8 and 9 show the deleterious effect of aqueous surfactant.

Figure 10:
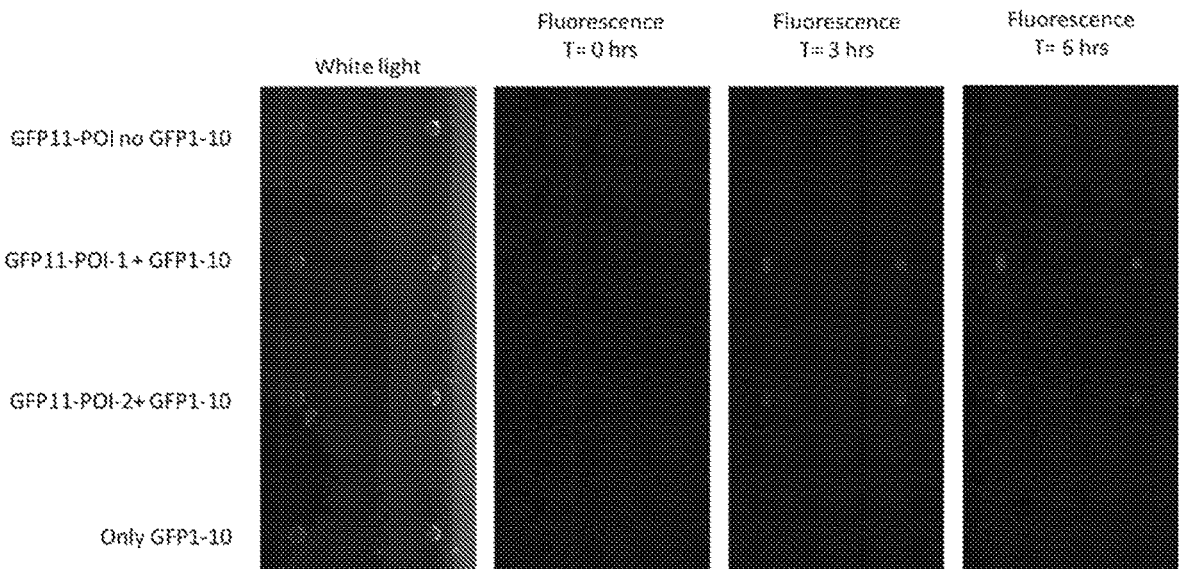
FIG. 10 Images extracted from a time course experiment whereby droplets of cell free protein synthesis (CFPS) lysate, optionally with a DNA construct for a protein of interest (POI—which here is either a variant of TdT or a viral Mpro protease tagged with a GFP11 peptide) and/or with a DNA construct for GFP1-10 polypeptide, were incubated on a digital microfluidic device for 6 hours and imaged periodically. Only the droplets containing lysate, DNA constructs for the GFP11-tagged POI and the GFP1-10 polypeptide show a significant increase in fluorescence over the course of the experiment, as seen in the right-hand column of images. Lysates which had DNA for only GFP1-10 or the POI alone did not show an increase in fluorescence.
Figure 11:
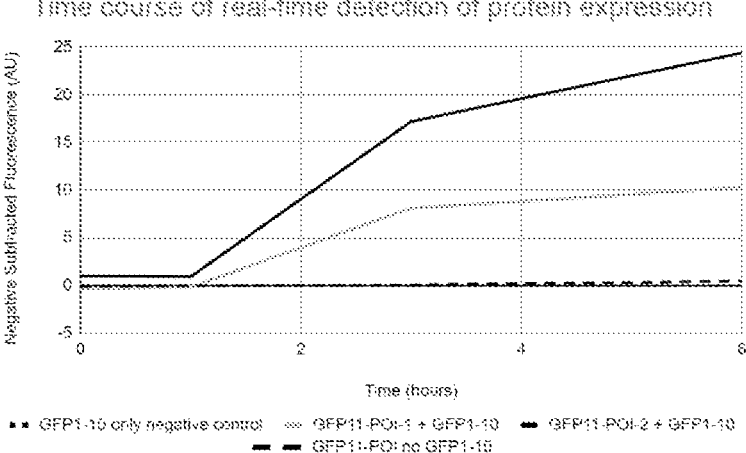
FIG. 11: A chart showing the real-time fluorescence increase seen in the droplets present in FIG. 10 (as well as a T=1 hour time point, which is similar to T=0 hour and was not included in FIG. 10). Quantification of fluorescence was performed in Image) and the values presented have been subject to normalisation by subtracting the background fluorescence seen in droplets of CFPS lysate and GFP1-10 (i.e. no POI DNA construct so no protein of interest, POI, expressed). Only the droplets containing all components—lysate, DNA constructs for both POI and GFP1-10 polypeptide—generate fluorescence over background.
Figure 12:
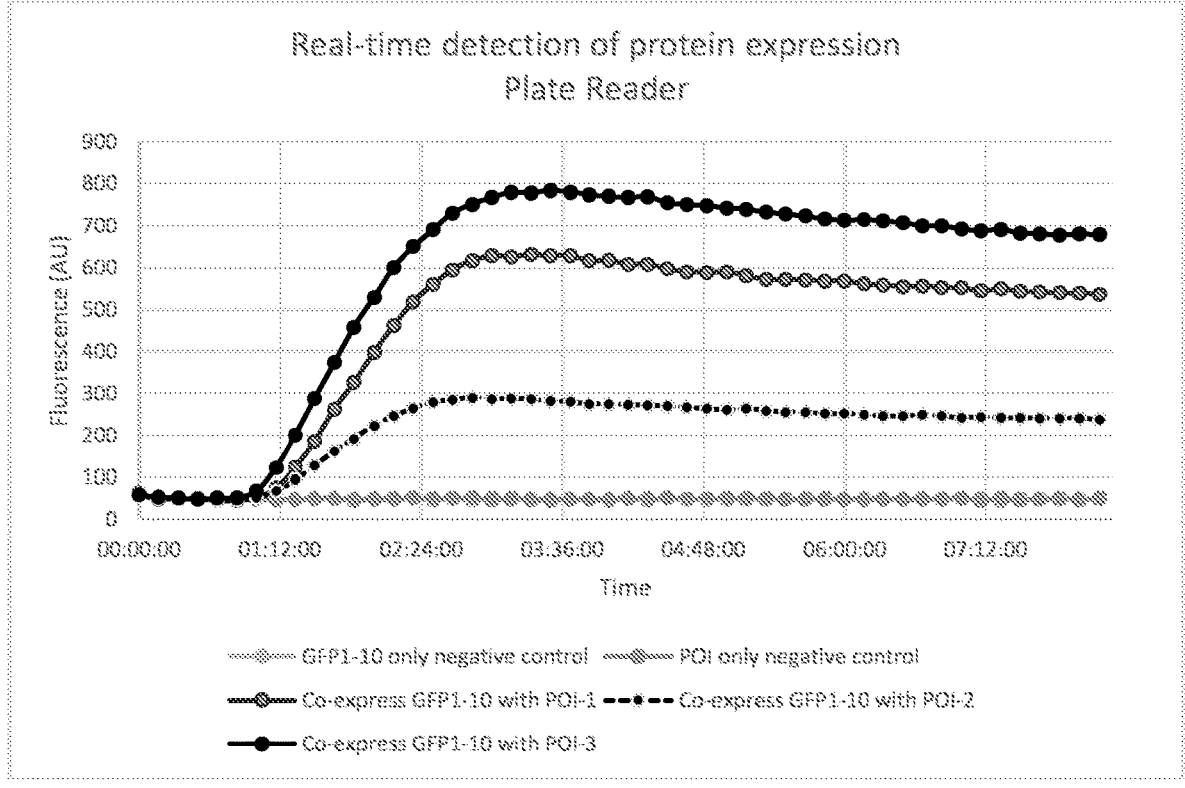
FIG. 12: A chart showing the real-time fluorescence of protein expression measured in a plate reader. DNA constructs for three different POIs (1: a TdT variant with a GFP11 peptide tag, 2: a TdT variant with a different GFP11 peptide tag, 3: a viral Mpro protease with a GFP11 peptide tag) were co-expressed with DNA constructs for GFP1-10 in cell free protein synthesis (CFPS) lysate. Only the lysates which had DNA constructs for both the GFP11-tagged POI and the GFP1-10 showed an increase in fluorescence over time, whereas the lysates with DNA for only GFP1-10 or GFP11-tagged POI did not.

FIGS. 10-12 show real time protein expression detection through co-expression of the detector (GFP1-10) with the GFP11-tagged protein of interest, in tubes and in droplets.

The invention claimed is:

1. A method for the monitoring of cell free protein synthesis in a droplet on a digital microfluidic device comprising:
   a. cell free transcription and translation of a protein of interest fused to a peptide tag where the peptide tag is a component of a fluorescent protein; and
   b. monitoring, in the digital microfluidic device, the presence of the peptide tag using a further polypeptide, said further polypeptide being a complementary portion of the fluorescent protein, which in the presence of the peptide tag produces a detectable signal; wherein the droplets are in an oil layer and the oil layer contains surfactant.

2. The method as claimed in claim 1, wherein the transcription and translation occurs in human lysate system.

3. The method as claimed in claim 1, wherein the transcription and translation occurs in a rabbit reticulocyte lysate (RRL) system or a Chinese Hamster Ovary lysate system.

4. The method as claimed in claim 1, wherein the cell free transcription and translation occurs in a wheat germ cell-free system.

5. The method as claimed in claim 1, wherein herein the cell free transcription and translation occurs a E. coli whole cell lysate system.

6. The method as claimed in claim 1, wherein the cell free transcription and translation occurs in a system of purified recombinant elements (PURE).

7. The method as claimed in claim 1, wherein the cell free transcription and translation are coupled.

8. The method as claimed in claim 1, wherein the cell free transcription and translation are uncoupled.

9. The method as claimed in claim 1, wherein the peptide tag is one component of a green fluorescent protein (GFP) or one component of sfCherry.

10. The method as claimed in claim 9 wherein the peptide tag is $GFP_{11}$ and the further polypeptide is $GFP_{1-10}$ or wherein the peptide tag is sfCherry11 and the further polypeptide is $sfCherry_{1-10}$.

11. The method as claimed in claim 1, wherein the protein of interest is fused to multiple peptide tags.

12. The method as claimed in claim 11 wherein the protein of interest is fused to multiple $GFP_{11}$ peptide tags or multiple $sfCherry_{11}$ peptide tags.

13. The method as claimed in claim 11, wherein the protein of interest is fused to one or more $sfCherry_{11}$ peptide tags and one or more $GFP_{11}$ peptide tags.

14. The method as claimed in claim 11, wherein the multiple peptide tags are fused to the peptide of interest in a tandem fashion.

15. The method as claimed in claim 1, wherein the protein of interest is a single.

16. The method as claimed in claim 15, wherein the single protein of interest is a TdT, IFN beta 1-alpha, VEGF or is a protein part of a protein-protein complex or larger assembly.

17. The method of claim 1, wherein the surfactant in the oil layer is a non-ionic surfactant.

18. The method according to claim 1, wherein the surfactant is a sorbitan ester.

19. The method according to claim 18, wherein the surfactant is sorbitan trioleate.

20. The method as claimed in claim 16, wherein the protein of interest is a terminal deoxynucleotidyl transferase (TdT) enzyme or a truncated version thereof or the homologous amino acid sequence of a terminal deoxynucleotidyl transferase (TdT) enzyme in other species or the homologous amino acid sequence of Polμ, Polβ, Polλ, and Polθ of any species or the homologous amino acid sequence of X family polymerases of any species.

* * * * *

SEQUENCE LISTING

<160> NUMBER OF SEQ ID NOS: 12

<210> SEQ ID NO 1
<211> LENGTH: 403
<212> TYPE: PRT
<213> ORGANISM: Artificial Sequence
<220> FEATURE:
<223> OTHER INFORMATION: GFP11_TdT fusion protein sequence

<400> SEQUENCE: 1

```
Met Lys Arg Asp His Met Val Leu His Glu Tyr Val Asn Ala Ala Gly
1               5                   10                  15

Ile Thr Gly Ser Gly Gly Ser Gly Gly Lys Phe Met His His His His
            20                  25                  30

His His Met Glu Asn Leu Tyr Phe Gln Gly Lys Ile Ser Gln Tyr Ala
        35                  40                  45

Cys Gln Arg Lys Thr Thr Leu Asn Asn Tyr Asn His Ile Phe Thr Asp
    50                  55                  60

Ala Phe Glu Ile Leu Ala Glu Asn Ser Glu Phe Lys Glu Asn Glu Val
65                  70                  75                  80

Ser Tyr Val Thr Phe Met Arg Ala Ala Ser Val Leu Lys Ser Leu Pro
                85                  90                  95

Phe Thr Ile Ile Ser Met Lys Asp Thr Glu Gly Ile Pro Cys Leu Gly
            100                 105                 110

Asp Lys Val Lys Cys Ile Ile Glu Glu Ile Ile Glu Asp Gly Glu Ser
        115                 120                 125

Ser Glu Val Lys Ala Val Leu Asn Asp Glu Arg Tyr Gln Ser Phe Lys
    130                 135                 140

Leu Phe Thr Ser Val Phe Gly Val Gly Leu Lys Thr Ser Glu Lys Trp
145                 150                 155                 160

Phe Arg Met Gly Phe Arg Ser Leu Ser Lys Ile Met Ser Asp Lys Thr
                165                 170                 175

Leu Lys Phe Thr Lys Met Gln Lys Ala Gly Phe Leu Tyr Tyr Glu Asp
            180                 185                 190

Leu Val Ser Cys Val Thr Arg Ala Glu Ala Glu Ala Val Gly Val Leu
        195                 200                 205

Val Lys Glu Ala Val Trp Ala Phe Leu Pro Asp Ala Phe Val Thr Met
    210                 215                 220

Thr Gly Gly Phe Arg Arg Gly Lys Lys Ile Gly His Asp Val Asp Phe
225                 230                 235                 240

Leu Ile Thr Ser Pro Gly Ser Ala Glu Asp Glu Glu Gln Leu Leu Pro
                245                 250                 255

Lys Val Ile Asn Leu Trp Glu Lys Lys Gly Leu Leu Leu Tyr Tyr Asp
            260                 265                 270

Leu Val Glu Ser Thr Phe Glu Lys Phe Lys Leu Pro Ser Arg Gln Val
        275                 280                 285

Asp Thr Leu Asp His Phe Gln Lys Cys Phe Leu Ile Leu Lys Leu His
    290                 295                 300

His Gln Arg Val Asp Ser Ser Lys Ser Asn Gln Gln Glu Gly Lys Thr
305                 310                 315                 320

Trp Lys Ala Ile Arg Val Asp Leu Val Met Cys Pro Tyr Glu Asn Arg
                325                 330                 335

Ala Phe Ala Leu Leu Gly Trp Thr Gly Ser Arg Gln Phe Glu Arg Asp
            340                 345                 350

Ile Arg Arg Tyr Ala Thr His Glu Arg Lys Met Met Leu Asp Asn His
```

-continued

```
          355              360              365

Ala Leu Tyr Asp Lys Thr Lys Arg Val Phe Leu Lys Ala Glu Ser Glu
    370              375              380

Glu Glu Ile Phe Ala His Leu Gly Leu Asp Tyr Ile Glu Pro Trp Glu
385              390              395              400

Arg Asn Ala

<210> SEQ ID NO 2
<211> LENGTH: 214
<212> TYPE: PRT
<213> ORGANISM: Artificial Sequence
<220> FEATURE:
<223> OTHER INFORMATION: sfGFG GFP1-10 polypeptide AA sequence

<400> SEQUENCE: 2

Met Ser Lys Gly Glu Glu Leu Phe Thr Gly Val Val Pro Ile Leu Val
1               5              10              15

Glu Leu Asp Gly Asp Val Asn Gly His Lys Phe Ser Val Arg Gly Glu
            20              25              30

Gly Glu Gly Asp Ala Thr Asn Gly Lys Leu Thr Leu Lys Phe Ile Cys
        35              40              45

Thr Thr Gly Lys Leu Pro Val Pro Trp Pro Thr Leu Val Thr Thr Leu
    50              55              60

Thr Tyr Gly Val Gln Cys Phe Ser Arg Tyr Pro Asp His Met Lys Arg
65              70              75              80

His Asp Phe Phe Lys Ser Ala Met Pro Glu Gly Tyr Val Gln Glu Arg
            85              90              95

Thr Ile Ser Phe Lys Asp Asp Gly Thr Tyr Lys Thr Arg Ala Glu Val
            100             105             110

Lys Phe Glu Gly Asp Thr Leu Val Asn Arg Ile Glu Leu Lys Gly Ile
        115             120             125

Asp Phe Lys Glu Asp Gly Asn Ile Leu Gly His Lys Leu Glu Tyr Asn
    130             135             140

Phe Asn Ser His Asn Val Tyr Ile Thr Ala Asp Lys Gln Lys Asn Gly
145             150             155             160

Ile Lys Ala Asn Phe Lys Ile Arg His Asn Val Glu Asp Gly Ser Val
            165             170             175

Gln Leu Ala Asp His Tyr Gln Gln Asn Thr Pro Ile Gly Asp Gly Pro
        180             185             190

Val Leu Leu Pro Asp Asn His Tyr Leu Ser Thr Gln Ser Val Leu Ser
        195             200             205

Lys Asp Pro Asn Glu Lys
    210

<210> SEQ ID NO 3
<211> LENGTH: 214
<212> TYPE: PRT
<213> ORGANISM: Artificial Sequence
<220> FEATURE:
<223> OTHER INFORMATION: Mutated sfGFP GFP1-10 polynucleotide AA
      sequence

<400> SEQUENCE: 3

Met Ser Lys Gly Glu Glu Leu Phe Thr Gly Val Val Pro Ile Leu Val
1               5              10              15

Glu Leu Asp Gly Asp Val Asn Gly His Lys Phe Ser Val Arg Gly Glu
            20              25              30
```

-continued

```
Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
                100                 105                 110

Lys Phe Glu Gly Asp Thr Leu Val Asn Arg Ile Glu Leu Lys Gly Thr
            115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
            195                 200                 205

Lys Asp Pro Asn Glu Lys
    210
```

```
<210> SEQ ID NO 4
<211> LENGTH: 19
<212> TYPE: PRT
<213> ORGANISM: Artificial Sequence
<220> FEATURE:
<223> OTHER INFORMATION: GFP11 1.0 sequence

<400> SEQUENCE: 4

Lys Arg Asp His Met Val Leu Leu Glu Phe Val Thr Ala Ala Gly Ile
1               5                   10                  15

Thr Gly Thr
```

```
<210> SEQ ID NO 5
<211> LENGTH: 19
<212> TYPE: PRT
<213> ORGANISM: Artificial Sequence
<220> FEATURE:
<223> OTHER INFORMATION: GFP11 2.0 sequence

<400> SEQUENCE: 5

Lys Arg Asp His Met Val Leu His Glu Phe Val Thr Ala Ala Gly Ile
1               5                   10                  15

Thr Gly Thr
```

```
<210> SEQ ID NO 6
<211> LENGTH: 17
<212> TYPE: PRT
<213> ORGANISM: Artificial Sequence
<220> FEATURE:
<223> OTHER INFORMATION: GFP11 3.0 sequence

<400> SEQUENCE: 6

Lys Arg Asp His Met Val Leu His Glu Ser Val Asn Ala Ala Gly Ile
1               5                   10                  15
```

-continued

Thr

<210> SEQ ID NO 7
<211> LENGTH: 16
<212> TYPE: PRT
<213> ORGANISM: Artificial Sequence
<220> FEATURE:
<223> OTHER INFORMATION: GFP11 4.0 sequence

<400> SEQUENCE: 7

Arg Asp His Met Val Leu His Glu Tyr Val Asn Ala Ala Gly Ile Thr
1               5                   10                  15

<210> SEQ ID NO 8
<211> LENGTH: 208
<212> TYPE: PRT
<213> ORGANISM: Artificial Sequence
<220> FEATURE:
<223> OTHER INFORMATION: sfCherry1-10 polypeptide AA sequence

<400> SEQUENCE: 8

Met Glu Glu Asp Asn Met Ala Ile Ile Lys Glu Phe Met Arg Phe Lys
1               5                   10                  15

Val His Met Glu Gly Ser Val Asn Gly His Glu Phe Glu Ile Glu Gly
            20                  25                  30

Glu Gly Glu Gly His Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Leu Lys Leu Ser Phe Pro Glu Gly Phe Thr Trp Glu Arg
                85                  90                  95

Val Met Asn Phe Glu Asp Gly Gly Val Val Thr Val Thr Gln Asp Ser
                100                 105                 110

Ser Leu Gln Asp Gly Glu Phe Ile Tyr Lys Val Lys Leu Leu Gly Thr
        115                 120                 125

Asn Phe Pro Ser Asp Gly Pro Val Met Gln Lys Lys Thr Met Gly Trp
        130                 135                 140

Glu Ala Ser Thr Glu Arg Met Tyr Pro Glu Asp Gly Ala Leu Lys Gly
145                 150                 155                 160

Glu Ile Asn Gln Arg Leu Lys Leu Lys Asp Gly Gly His Tyr Asp Ala
                165                 170                 175

Glu Val Lys Thr Thr Tyr Lys Ala Lys Lys Pro Val Gln Leu Pro Gly
                180                 185                 190

Ala Tyr Asn Val Asp Ile Lys Leu Asp Ile Thr Ser His Asn Glu Asp
        195                 200                 205

<210> SEQ ID NO 9
<211> LENGTH: 18
<212> TYPE: PRT
<213> ORGANISM: Artificial Sequence
<220> FEATURE:
<223> OTHER INFORMATION: sfCherry11 sequence

<400> SEQUENCE: 9

Tyr Thr Ile Val Glu Gln Tyr Glu Arg Ala Glu Gly Arg His Ser Thr
1               5                   10                  15

Gly Gly

-continued

```
<210> SEQ ID NO 10
<211> LENGTH: 114
<212> TYPE: PRT
<213> ORGANISM: Artificial Sequence
<220> FEATURE:
<223> OTHER INFORMATION: NFAST sequence

<400> SEQUENCE: 10

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
            35                  40                  45

Ile Thr Gly Arg Asp Pro Lys Gln Val Ile Gly Lys Asn Phe Phe Lys
    50                  55                  60

Asp Val Ala Pro Gly Thr Asp Ser Pro Glu Phe Tyr Gly Lys Phe Lys
65                  70                  75                  80

Glu Gly Val Ala Ser Gly Asn Leu Asn Thr Met Phe Glu Trp Met Ile
                85                  90                  95

Pro Thr Ser Arg Gly Pro Thr Lys Val Lys Val His Met Lys Lys Ala
            100                 105                 110

Leu Ser

<210> SEQ ID NO 11
<211> LENGTH: 11
<212> TYPE: PRT
<213> ORGANISM: Artificial Sequence
<220> FEATURE:
<223> OTHER INFORMATION: CFAST11 sequence

<400> SEQUENCE: 11

Gly Asp Ser Tyr Trp Val Phe Val Lys Arg Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: CFAST10 sequence

<400> SEQUENCE: 12

Gly Asp Ser Tyr Trp Val Phe Val Lys Arg
1               5                   10
```